(12) United States Patent
Garai et al.

(10) Patent No.: US 12,722,018 B2
(45) Date of Patent: Sep. 1, 2026

(54) DEVICES AND METHODS FOR RETENTION OF TEMPORARY PACING LEADS

(71) Applicant: Merit Medical Systems, Inc., South Jordan, UT (US)

(72) Inventors: Ellis Garai, Studio City, CA (US); Aravind Swaminathan, San Mateo, CA (US); Laura N. Dietch, Menlo Park, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 924 days.

(21) Appl. No.: 17/713,036

(22) Filed: Apr. 4, 2022

(65) Prior Publication Data

US 2022/0273958 A1 Sep. 1, 2022

Related U.S. Application Data

(63) Continuation of application No. PCT/US2020/054260, filed on Oct. 5, 2020.

(Continued)

(51) Int. Cl.
*A61N 1/375* (2006.01)
*A61N 1/05* (2006.01)
(Continued)

(52) U.S. Cl.
CPC ......... *A61N 1/37512* (2017.08); *A61N 1/056* (2013.01); *A61N 1/059* (2013.01);
(Continued)

(58) Field of Classification Search
CPC .... A61N 1/37512; A61N 1/056; A61N 1/059; A61N 1/3625; A61N 1/37205;
(Continued)

(56) References Cited

U.S. PATENT DOCUMENTS 5,334,045 A 8/1994 Cappa et al.
5,637,417 A 6/1997 Engmark et al.
(Continued)

FOREIGN PATENT DOCUMENTS

JP 3127893 B2 11/2006
JP 2013537835 A 10/2013
(Continued)

OTHER PUBLICATIONS

International Search Report and Written Opinion for PCT/US2020/054260 on Feb. 9, 2021.

(Continued)

*Primary Examiner* — Eugene T Wu
(74) *Attorney, Agent, or Firm* — Dorsey & Whitney LLP

(57) ABSTRACT

A temporary pacing lead device comprises: an elongate body having a distal portion and a proximal end; an electrode array at the distal portion configured to deliver a pacing signal to target tissue; a displacement member attached to a first side of the distal portion; at least one anchoring element deployable from a second opposite side; and an interface at the proximal end of the elongate body. The interface is configured to couple to a pacing signal generator and/or a control handle to actuate the displacement member and/or anchoring element. The pacing generator can be a miniature pacing signal generator and/or a standard pacemaker device, and the interface can switch between providing the pacing signal from either of the two sources. The miniature pacing signal generator can include a protective element for the control and/or actuation elements at the proximal end.

24 Claims, 38 Drawing Sheets

Related U.S. Application Data

(60) Provisional application No. 62/942,441, filed on Dec. 2, 2019, provisional application No. 62/924,118, filed on Oct. 21, 2019.

(51) Int. Cl.
*A61N 1/362* (2006.01)
*A61N 1/372* (2006.01)

(52) U.S. Cl.
CPC ....... *A61N 1/3625* (2013.01); *A61N 1/37205* (2013.01); *A61N 1/37518* (2017.08); *A61N 1/3752* (2013.01); *A61N 1/3756* (2013.01)

(58) Field of Classification Search
CPC .............. A61N 1/37518; A61N 1/3752; A61N 1/3756; A61N 1/0595; A61N 2001/0578; A61N 1/0573
See application file for complete search history.

(56) References Cited

U.S. PATENT DOCUMENTS

| | | | | |
|---|---|---|---|---|
| 5,843,132 | A | 12/1998 | Ilvento | |
| 9,844,663 | B2 | 12/2017 | Swaminathan et al. | |
| 9,855,421 | B2 | 1/2018 | Garai et al. | |
| 9,872,981 | B2 | 1/2018 | Sparks et al. | |
| 10,124,162 | B2 | 11/2018 | Garai et al. | |
| 10,232,170 | B2 | 3/2019 | Sparks et al. | |
| 10,953,223 | B2 | 3/2021 | Sparks et al. | |
| 2006/0106445 | A1 | 5/2006 | Woollett | |
| 2012/0041508 | A1 | 2/2012 | Rousso et al. | |
| 2012/0078336 | A1 | 3/2012 | Helland | |
| 2012/0311092 | A1* | 12/2012 | Musiol | G16H 40/67 709/219 |
| 2012/0323253 | A1* | 12/2012 | Garai | A61N 1/057 606/129 |
| 2016/0166825 | A1 | 6/2016 | Henschel et al. | |
| 2018/0221654 | A1* | 8/2018 | Hess | A61N 1/3625 |
| 2019/0038893 | A1 | 2/2019 | Garai et al. | |
| 2020/0147403 | A1* | 5/2020 | Manicka | A61N 1/059 |
| 2021/0236812 | A1 | 8/2021 | Sparks et al. | |
| 2023/0405344 | A1 | 12/2023 | Garai et al. | |

FOREIGN PATENT DOCUMENTS

| | | | |
|---|---|---|---|
| JP | 2016154664 | A | 9/2016 |
| JP | 2017519608 | A | 7/2017 |
| JP | 2017523867 | A | 8/2017 |
| WO | 2015172023 | A2 | 11/2015 |
| WO | WO-2021080765 | A1 | 4/2021 |

OTHER PUBLICATIONS

Extended European Search Report dated Oct. 25, 2023 for EP20879087.3.

International Search Report and Written Opinion dated Feb. 9, 2021 for PCT/US2020/054260.

Office Action dated Mar. 24, 2025 for U.S. Appl. No. 18/458,941.

Office Action dated Oct. 16, 2025 for U.S. Appl. No. 18/458,941.

Notice of Allowance dated Apr. 14, 2026 for U.S. Appl. No. 18/458,941.

* cited by examiner

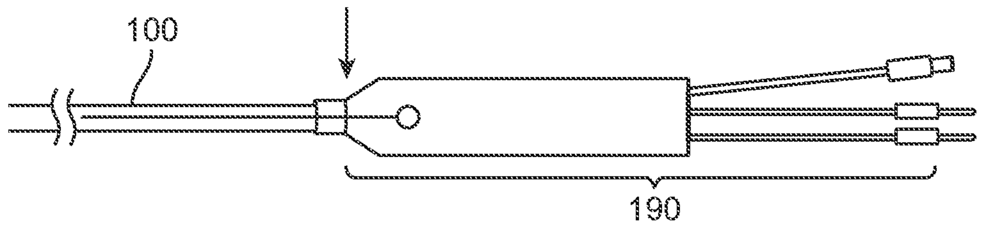
FIG. 8A
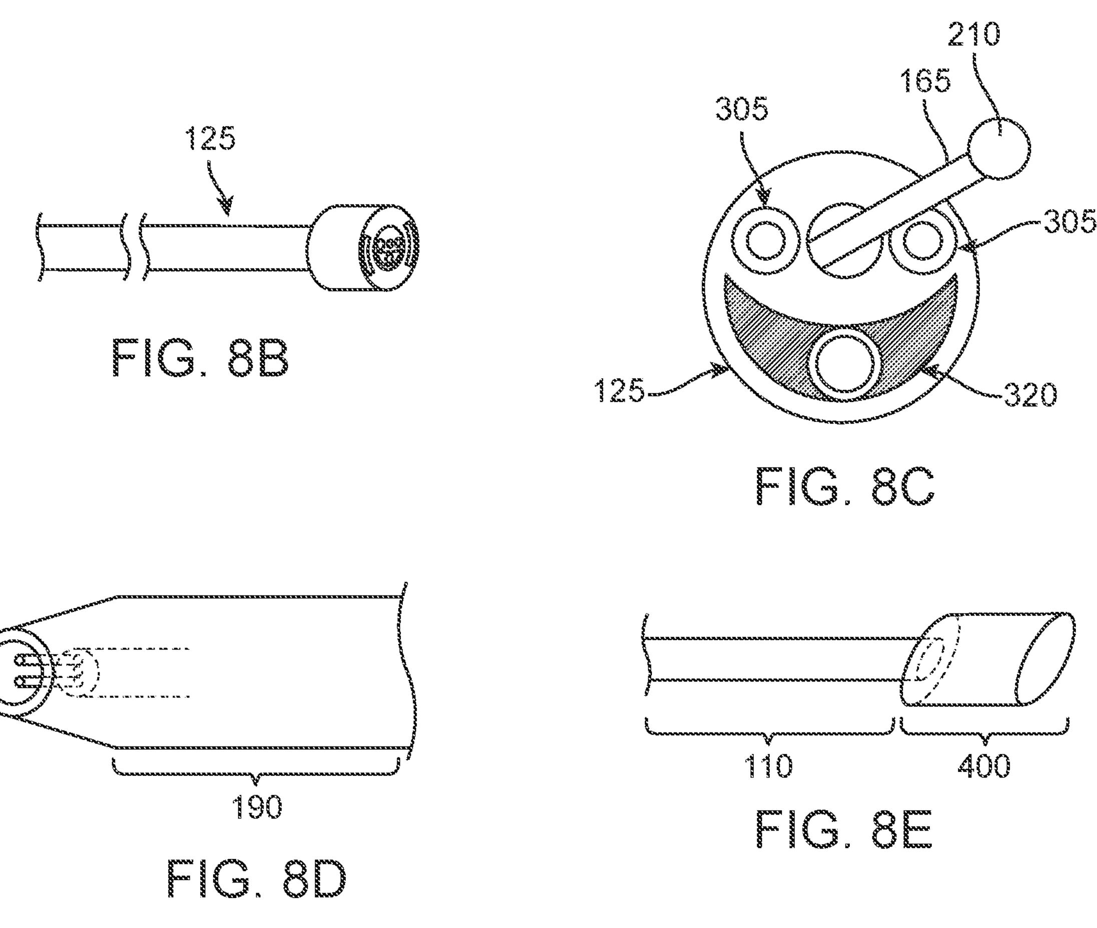
FIG. 8B
FIG. 8C
FIG. 8D
FIG. 8E
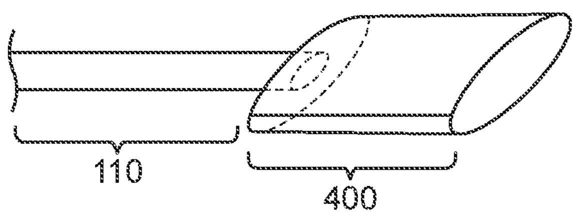
FIG. 8F

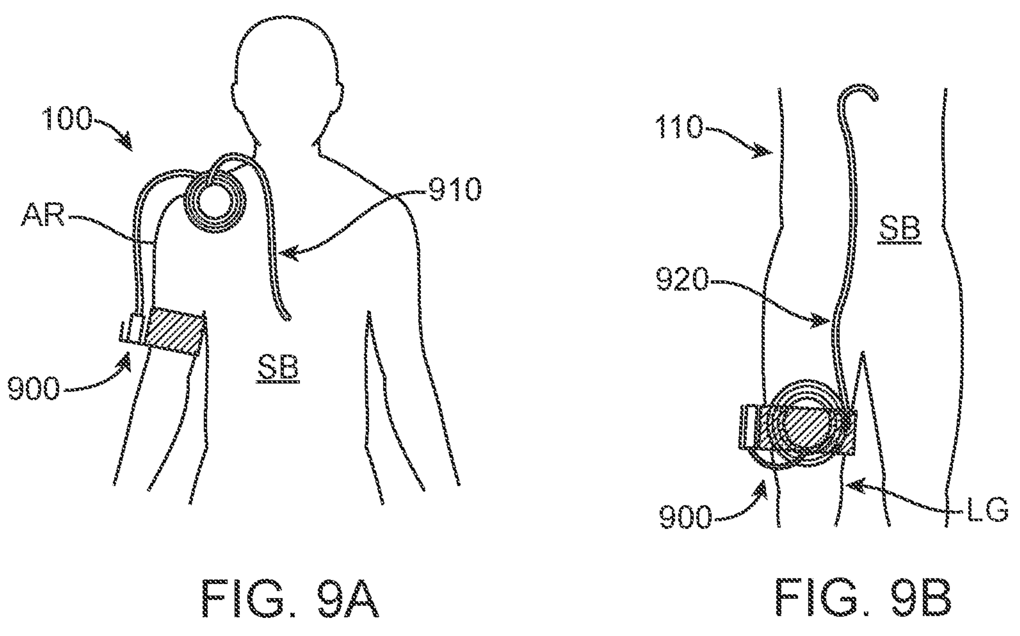
FIG. 9A
FIG. 9B
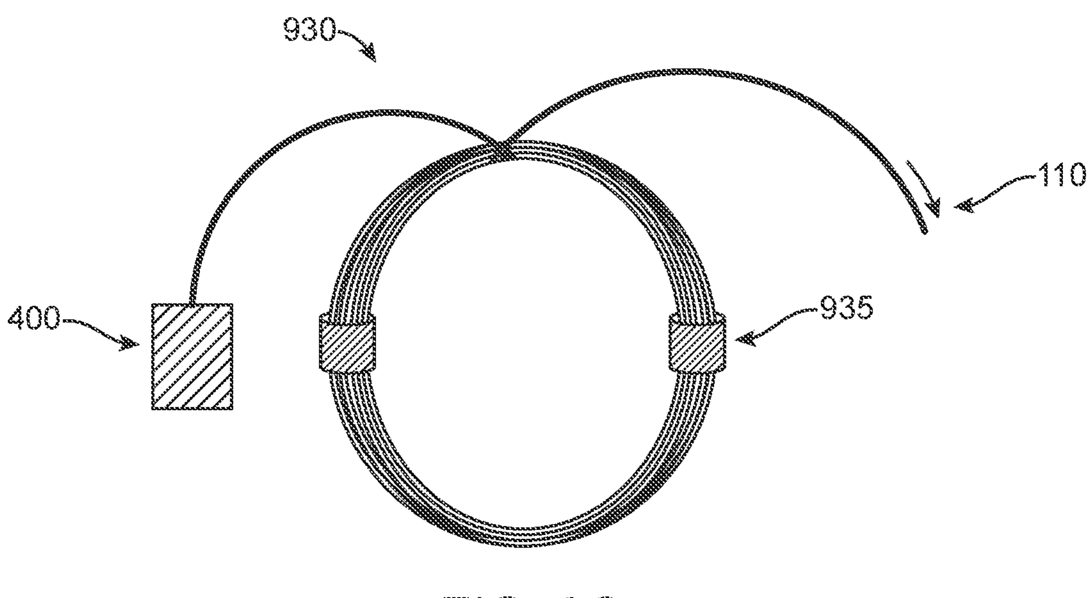
FIG. 9C

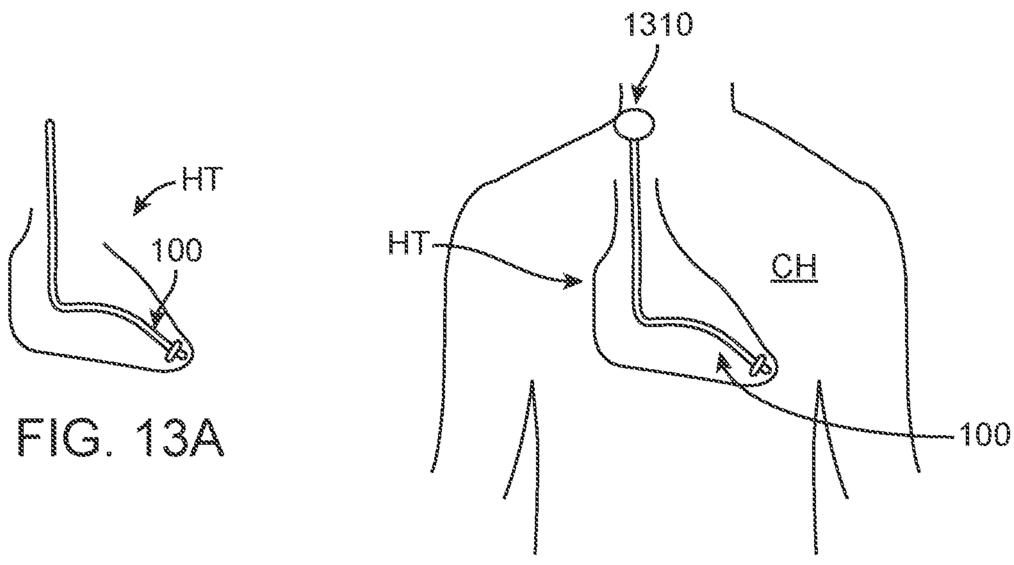
FIG. 13A
FIG. 13B
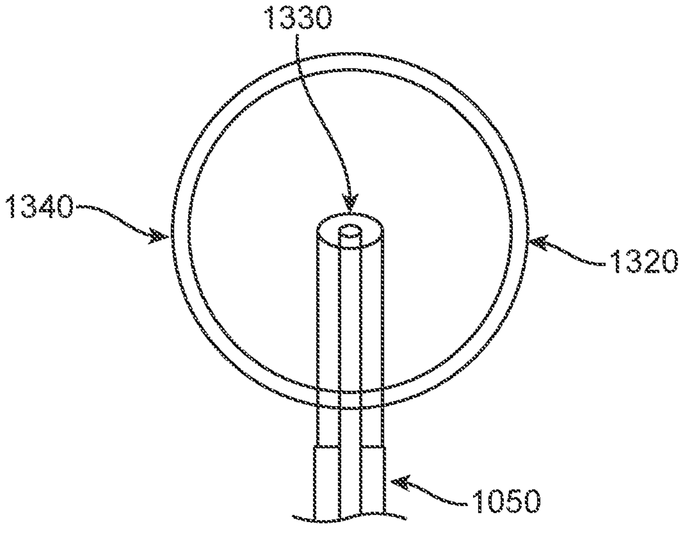
FIG. 13C

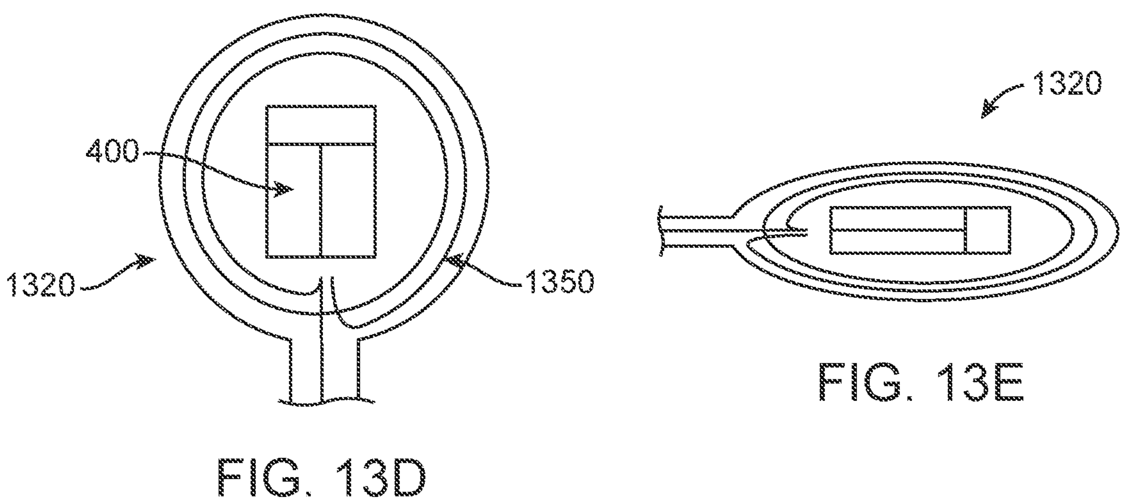
FIG. 13D
FIG. 13E
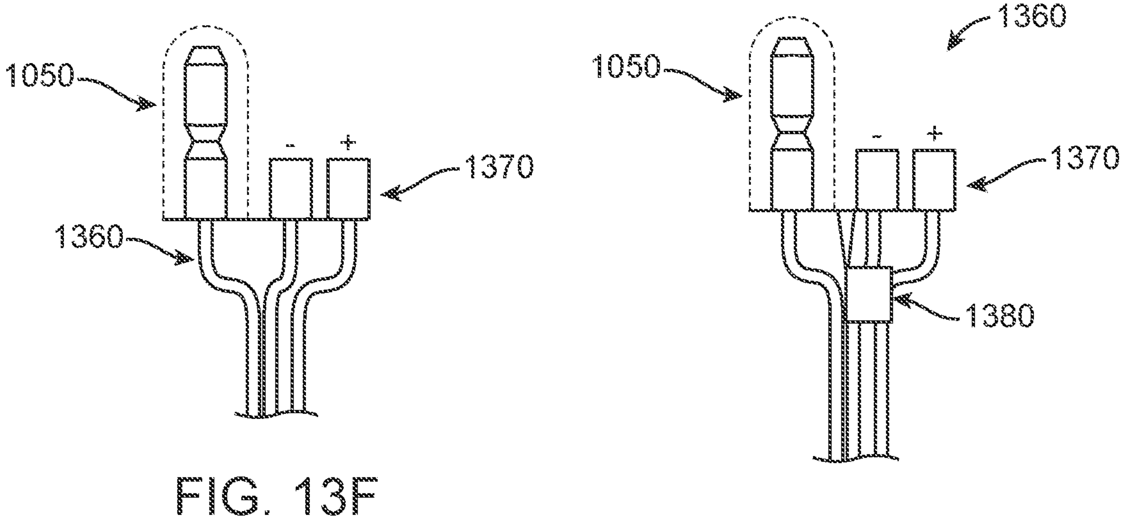
FIG. 13F
FIG. 13G 110
110
110
1405
1405
400
190
190n
190n
190
400

110
1405
1520sp
1520s
1615
190
1370a
1370c
1620
1525
1625
1630

235
235
165
1545
110
175

110
18C
18C
175
175t
1405
190
1520s
1405p 110
1405
1520sp
1520s
2115
190
220p
1370a
1370c 110
2205
1410
2120
2120
2125

110
2130
2125

110
1050
1415
2135

DEVICES AND METHODS FOR RETENTION OF TEMPORARY PACING LEADS

CROSS-REFERENCE

This application is a continuation of PCT Application No. PCT/US20/54260, filed Oct. 5, 2020; which claims priority to U.S. Provisional Application Nos. 62/924,118, filed Oct. 21, 2019, and 62/942,441, filed Dec. 2, 2019; the contents of which are incorporated by reference.

The subject matter of this patent application is related to the subject matter of the following patents and patent applications: U.S. patent application Ser. No. 13/219,874, now U.S. Pat. No. 9,855,421, U.S. patent application Ser. No. 14/708,792, now U.S. Pat. No. 9,844,663, U.S. patent application Ser. No. 15/691,187, now U.S. Pat. No. 10,124, 162, U.S. patent application Ser. No. 16/148,357, U.S. patent application Ser. No. 14/707,246, now U.S. Pat. No. 9,872,981, U.S. patent application Ser. No. 15/844,367, now U.S. Pat. No. 10,232,170, and U.S. patent application Ser. No. 16/256,473, which are incorporated herein by reference.

BACKGROUND

The present disclosure relates generally to the electrode stimulation device field, and more specifically to devices and methods for retention of temporary pacing leads positioned in a subject's body for an extended period of time. The devices and methods disclosed herein may be particularly useful for temporary cardiac pacing leads which may be placed in a ventricle or other chamber of the heart, which may anchor to cardiac tissue with anchor structures that also serve as electrodes, and which may be placed against the epicardium of the heart, to name a few applications.

The temporary cardiac pacing leads described herein may be placed during a cardiac procedure and retained in a cardiac chamber or against the pericardium for an extended period of time after the procedure, such as the period of time until the placement of a permanent pacing device or until the heart has recovered its normal or close to normal heart rate and/or beating cycle. Examples of such procedures include but are not limited to transcatheter aortic valve replacement (TAVR), transcatheter mitral valve repair (TMVR), and transcatheter mitral valve replacement procedures. The temporary cardiac pacing leads described herein may also be used to treat patients with bradycardia (reduced heart rate), often with reversible causes and which would not require permanent pacing device.

SUMMARY

Devices and methods for retention of temporary pacing leads positioned in a subject's body are described herein. Temporary pacing leads may be advanced into a patient or subject's heart to pace the heart during and after various cardiac procedures, or as standalone therapy. The temporary pacing lead may exit from the body of the patient via an access site, such as to the femoral vein, femoral artery, carotid artery, or jugular artery access site, and the portion of the temporary pacing lead exiting the body may couple to a signal generator. These signal generators are typically bulky, thereby restricting ambulation, particularly to outside of a hospital setting. Disclosed herein are miniature pacing signal generators configured to couple to the proximal ends of temporary pacing leads. These miniature pacing signal generators are small and minimally obstructive such that a patient implanted with a temporary pacing lead can leave the hospital or clinic until such a time the temporary pacing lead can be removed upon a return visit. The miniature pacing signal generators may be external to the body or can be placed under the skin surface, i.e., subcutaneous.

Further disclosed herein are retention elements for these miniature pacing signal generators and/or the proximal ends of temporary pacing lead to hold these relative to the body of the subject in a safe, clean, and non-obstructive manner. These retention elements may be in the form of patches, adhesive patches, bands, wrists bands, arm bands, leg bands, and straps, to name a few examples. The retention elements may be configured and/or placed to minimize strain between the portion of the temporary pacing lead at the access site and the access site, thereby providing patient comfort for extended wear.

The use of the miniature pacing signal generators and/or the retention elements can allow a subject with an implanted temporary pacing lead to leave the hospital or clinic for an extended period of time before returning to the hospital or clinic for removal of the temporary pacing lead, reducing hospital or clinic time and costs. For instance, a temporary pacing lead may be used during a cardiac procedure, such as transcatheter aortic valve replacement (TAVR), transcatheter mitral valve repair (TMVR), and transcatheter mitral valve replacement procedures, and instead of implanting a permanent pacemaker after the procedure, the temporary pacing lead may be retained for a period of time until the patient's cardiac cycle has recovered its normal or close to normal heart rate and/or beating cycle. The patient may be allowed to leave the clinic and/or hospital for the recovery period, before returning for a procedure to remove the temporary pacing lead. Temporary pacing leads may be used between 1 to 180 days, typically between 1 to 30 days, such as between 5 to 10 days, and more specifically as 7 days (from implantation to removal, typically with the subject being able to leave the hospital and/or clinic between the time of implantation to the time of removal). In some embodiments, the temporary pacing lead may be used for more than 180 days.

The miniature pacing signal generators may comprise elements such as a power source, a signal generating element and/or processor, a signal recorder, a wireless communication transmitter and/or receiver, a protective element for control and/or actuation elements at the proximal end of the temporary pacing leads, and adapters for other devices, such as a standard adapter (e.g., IS-1) for a standard pacemaker device. The temporary pacing lead will typically be operable with a deployment or control handle that is often detachable. The deployment or control handle and/or the miniature pacing signal generator may include a control switch to set whether the pacing signal delivered to the subject is from a coupled pacemaker device via the standard adaptor or from the native pacing signal generator. For instance, the standard pacemaker device may provide the pacing signal to the patient while in the hospital and/or clinic before being switched to the miniature pacing signal generator when the patient leaves, or vice versa for the patient returning to the hospital and/or clinic.

Aspects of the present disclosure provide methods for positioning an electrode at target tissue of a patient's heart. An exemplary method may comprise the following steps. An elongate body having a distal portion and a proximal portion may be navigated to position an electrode array and at least one anchoring element carried on a side of the distal portion of the elongate body adjacent to the target tissue. After the distal portion of the elongate body has been positioned, the distal portion but not the proximal portion of the elongate body may be engaged against the target tissue to contact the electrode array and the at least one anchoring element against the target tissue. After engaging the distal portion of the elongate body against the target tissue, the at least one anchoring element on the side of the distal portion of the elongate body may be deployed to affix the at least one anchoring element to the target tissue. A pacing signal may be delivered to the target tissue with the electrode array. The distal portion of the elongate body may be retained as engaged against the target tissue for between 1 minute and 180 days.

In some embodiments, the distal portion of the elongate body is engaged against the target tissue between 1 and 180 days, such as for between 1 and 30 days and/or between 5 and 10 days.

In some embodiments, the method further comprises steps of retracting the at least one anchoring element, collapsing the displacement mechanism, and retracting the elongate body.

In some embodiments, a proximal portion of the elongate body extends out from the body of the patient after the distal portion of the elongate body is engaged against the target tissue. A control handle coupled to the proximal portion of the elongate body may be operated to deploy the at least one anchoring element. The control handle coupled to the proximal portion of the elongate body may be detached after the distal portion of the elongate body is engaged against the target tissue.

A miniature pacing signal generator may be coupled to the proximal end of the elongate body. The miniature pacing signal generator may be positioned subcutaneously.

A standard pacemaker device may be coupled to the proximal end of the elongate body. The standard pacemaker may be coupled to the proximal end of the elongate body with a standard interface. The standard interface may be an IS-1 interface.

A first pacing signal generator and a second pacing signal generator may be coupled to the proximal end of the elongate body. Delivery of a pacing signal may be switched between the first and the second pacing signal generator. The first pacing signal generator may comprise a miniature a standard connector interface (such as an international standard connector interface, for example, IS-1), and the second pacing signal generator may comprise a standard temporary external pacemaker device The first pacing signal generator with the standard connector interface may comprise a miniature pacing signal generator.

In some embodiments, electrical signals from the target tissue are recorded with the electrode array. The recorded electrical signals may be transmitted to a local computing device. The local computing device may be a mobile computing device of the patient. The local computing device may transmit the recorded electrical signals to a remote computing device. For example, a medical professional or caregiver may be notified with the remote computing device if the recorded electrical signals indicate an emergency or a clinically significant event. The remote computing device may be a cloud-based server. The recorded electrical signals may be forwarded to the medical professional or caregiver.

In some embodiments, a displacement mechanism attached to a side of the distal portion of the elongate body opposite to the side that carries the electrode array and the at least one anchoring element is actuated to engage the distal portion but not the proximal portion of the elongate body against the target tissue to contact the electrode array and the at least one anchoring element against the target tissue. A control handle coupled to the proximal portion of the elongate body may be operated to actuate the displacement mechanism.

In some embodiments, the target tissue is cardiac tissue accessible from a cardiac chamber or epicardium.

Aspects of the present disclosure provide further methods for positioning an electrode to target tissue of a patient's heart. An exemplary method may comprise the following steps. An elongate body having a distal portion and a proximal portion may be navigated to position an electrode array and at least one anchoring element carried on a side of the distal portion of the elongate body adjacent to a target tissue within the chamber or against the epicardium. After the distal portion of the elongate body has been positioned, the distal portion but not the proximal portion of the elongate body may be engaged against the target tissue to contact the electrode array and the at least one anchoring element against the target tissue. After actuating the displacement mechanism to engage the distal portion of the elongate body against the target tissue, the at least one anchoring element on the side of the distal portion of the elongate body may be deployed to affix the at least one anchoring element to the target tissue. A proximal portion of the elongate body may extend out from the body of the patient after the distal portion of the elongate body is engaged against the target tissue. A pacing signal may be delivered to the target tissue with the electrode array. Delivery of a pacing signal may be switched between the first and the second pacing signal generator. The first pacing signal generator may comprise a miniature pacing signal generator with a standard connector interface (such as an international standard connector interface, for example, IS-1), and the second pacing signal generator may comprise a standard temporary external pacemaker device The pacing signal generator with the standard connector interface may comprise a miniature pacing signal generator.

In some embodiments, the method further comprises steps of retracting the at least one anchoring element, collapsing the displacement mechanism, and retracting the elongate body. A control handle coupled to the proximal portion of the elongate body may be operated to deploy or retract the at least one anchoring element. The control handle coupled to the proximal portion of the elongate body may be detached after the distal portion of the elongate body is engaged against the target tissue.

In some embodiments, the signal generator or pacemaker is coupled to the proximal end of the elongate body with a standard interface, such as an IS-1 interface.

In some embodiments, a displacement mechanism attached to a side of the distal portion of the elongate body opposite to the side that carries the electrode array and the at least one anchoring element is actuated to engage the distal portion but not the proximal portion of the elongate body against the target tissue to contact the electrode array and the at least one anchoring element against the target tissue. A control handle coupled to the proximal portion of the elongate body may be operated to actuate the displacement mechanism.

In some embodiments, the target tissue is cardiac tissue accessible from a cardiac chamber or epicardium.

Aspects of the present disclosure provide further methods for positioning an electrode to a target tissue. An exemplary method may comprise the following steps. An elongate body having a distal portion and a proximal portion may be navigated to position an electrode array and at least one anchoring element carried on a side of the distal portion of the elongate body adjacent to a target tissue. The at least one anchoring element on the side of the distal portion of the elongate body may be deployed to affix the at least one anchoring element to the target tissue. A proximal portion of the elongate body may extend out from the body of the patient after the distal portion of the elongate body is engaged against the target tissue. A pacing signal may be delivered to the target tissue with the electrode array using a standard external pacing signal generator. A control handle coupled to the proximal portion of the elongate body may be detached. A miniature pacing signal generator or a standard pacemaker device may be coupled to the proximal end of the elongate body.

Aspects of the present disclosure may provide temporary pacing lead devices. An exemplary temporary pacing lead device may comprise an elongate body having a distal portion positionable at the target tissue of a subject and a proximal end, an array of electrodes at the distal portion and configured to deliver a pacing signal to target tissue, at least one anchoring element deployable from the distal portion, a displacement member at the distal portion, and an interface at the proximal end of the elongate body. The interface may be configured to couple to one or more of (i) a control handle to actuate one or more of the displacement member or the at least one anchoring element or (ii) a pacing signal generator.

In some embodiments, the pacing signal generator is one or more of (i) a miniature pacing signal generator or (ii) a standard pacemaker device.

In some embodiments, the interface is switchable to select the pacing signal from being provided from either (i) a miniature pacing signal generator or (ii) a standard pacemaker device.

In some embodiments, the pacing signal generator is the standard pacemaker device and the standard pacemaker device is coupled to the interface via an IS-1 connection.

In some embodiments, the pacing signal generator is the miniature pacing signal generator. The miniature pacing signal generator may comprise one or more of a power source, a signal generating element and/or processor, a signal recorder, a wireless communication transmitter and/or receiver, a protective element for control and/or actuation elements at the proximal end of the temporary pacing lead, or an adapter for a further device.

In some embodiments, the temporary pacing lead device further comprises a displacement member attached to a first side of the distal portion. The at least one anchoring element may be deployable from a second side of the distal portion opposite the first side.

Aspects of the present disclosure provide methods for pacing the heart. An exemplary method may comprise the following steps. An electrode array of a pacing device may be positioned at target tissue of a patient's heart. A distal portion of the pacing device, including the electrode array, may be retained as engaged against the target tissue for between 1 minute and 180 days. Pacing signals may be delivered to the target tissue with the electrode array. Electrical signals from the target tissue may be recorded with the pacing device. The recorded electrical signals may be transmitted to a local computing device. The recorded electrical signals may be transmitted to a remote computing device with the computing device. A medical professional or caregiver may be notified with the remote computing device if the recorded electrical signals indicate an emergency or a clinically significant event.

Aspects of the present disclosure provide further methods for pacing the heart. An exemplary method may comprise the following steps. A temporary pacing device may be advanced to target tissue of a heart of a patient. A deployment handle coupled to a proximal end of the temporary pacing lead may be operated to deploy at least one attachment member of the temporary pacing device and engage the temporary pacing lead against the target tissue. The deployment handle may be detached from the proximal end of the temporary pacing device. A miniature signal generator may be attached to the proximal end of the temporary pacing device. A pacing signal may be generated with the miniature signal generator. The generated pacing signal may be delivered to the target tissue with the temporary pacing lead.

In some embodiments, the miniature signal generator is removed from the proximal end of the temporary pacing device and the temporary pacing device is retracted from the target tissue. An attachment member actuation tool may be coupled to the proximal end of the temporary pacing device. The attachment member actuating tool may be actuated to retract the at least one attachment member from the target tissue.

In some embodiments, the miniature signal generator is positioned subcutaneously.

In some embodiments, the miniature signal generator is positioned against or adjacent skin of the patient with a retention element.

In some embodiments, the distal portion of the elongate body is retained as engaged against the target tissue for between 1 minute and 180 days.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 8A shows a side view of a proximal portion of a temporary pacing lead device with a detachable proximal handle attached, according to embodiments of the present disclosure;

FIG. 8B shows a side view of the proximal portion of the temporary pacing lead device of FIG. 8A with the detachable proximal handle detached, according to embodiments of the present disclosure;

FIG. 8C shows a cross-section of the proximal end of the temporary pacing lead device of FIG. 8A with the detachable proximal handle detached, according to embodiments of the present disclosure;

FIG. 8D shows a cut-away side view of the detached detachable proximal handle of FIG. 8A, according to embodiments of the present disclosure;

FIG. 8E shows a side view of the proximal portion of the temporary pacing lead device of FIG. 8A with the detachable proximal handle detached and a miniature pacing signal generator attached, according to embodiments of the present disclosure;

FIG. 8F shows a side view of the proximal portion of the temporary pacing lead device of FIG. 8A with the detachable proximal handle detached and another miniature pacing signal generator attached, according to embodiments of the present disclosure;

FIG. 9A shows a front schematic view of a subject with an implanted temporary pacing lead device with its proximal portion extending from the subject's body at a jugular vein access and retained on the subject with a retention band on the arm, according to embodiments of the present disclosure;

FIG. 9B shows a front schematic view of a subject with an implanted temporary pacing lead device with its proximal portion extending from the subject's body at a femoral vein access and retained on the subject with a retention band on the leg, according to embodiments of the present disclosure;

FIG. 9C shows a perspective view of a wire management element for temporary pacing lead devices, according to embodiments of the present disclosure;

FIGS. 12A-12C also show a standard adapter (e.g., IS-1) permanently attached to the lead body or the detachable handle or both.

FIG. 13A shows a side section view of a cardiac chamber of a heart with a temporary pacing lead device implanted therein, according to embodiments of the present disclosure;

FIG. 13B shows a front view of a chest of a subject, including a temporary pacing lead device with its distal working portion implanted in a cardiac chamber of the heart and its proximal control portion positioned near the neck, according to embodiments of the present disclosure;

FIGS. 13C and 13D show a top section view of a retention patch for the proximal control portion of a temporary pacing lead device extending from a subject's body, according to embodiments of the present disclosure;

FIG. 13E shows a side section view of a retention patch for the proximal control portion of a temporary pacing lead device extending from a subject's body, according to embodiments of the present disclosure;

FIGS. 13F and 13G show side views of an adapter at the proximal control portion of a temporary pacing lead device, according to embodiments of the present disclosure.

FIG. 18A shows a perspective section view; FIG. 18B shows a magnified perspective section view; FIG. 18C shows a cross-sectional view; and, FIG. 18D shows a perspective section view.

FIG. 20A shows a side, section view; FIG. 20B shows a perspective view; FIG. 20C shows a section view; and, FIG. 20D shows a magnified, cut-away view.

DETAILED DESCRIPTION

Figures 1A, 1B, 1C:
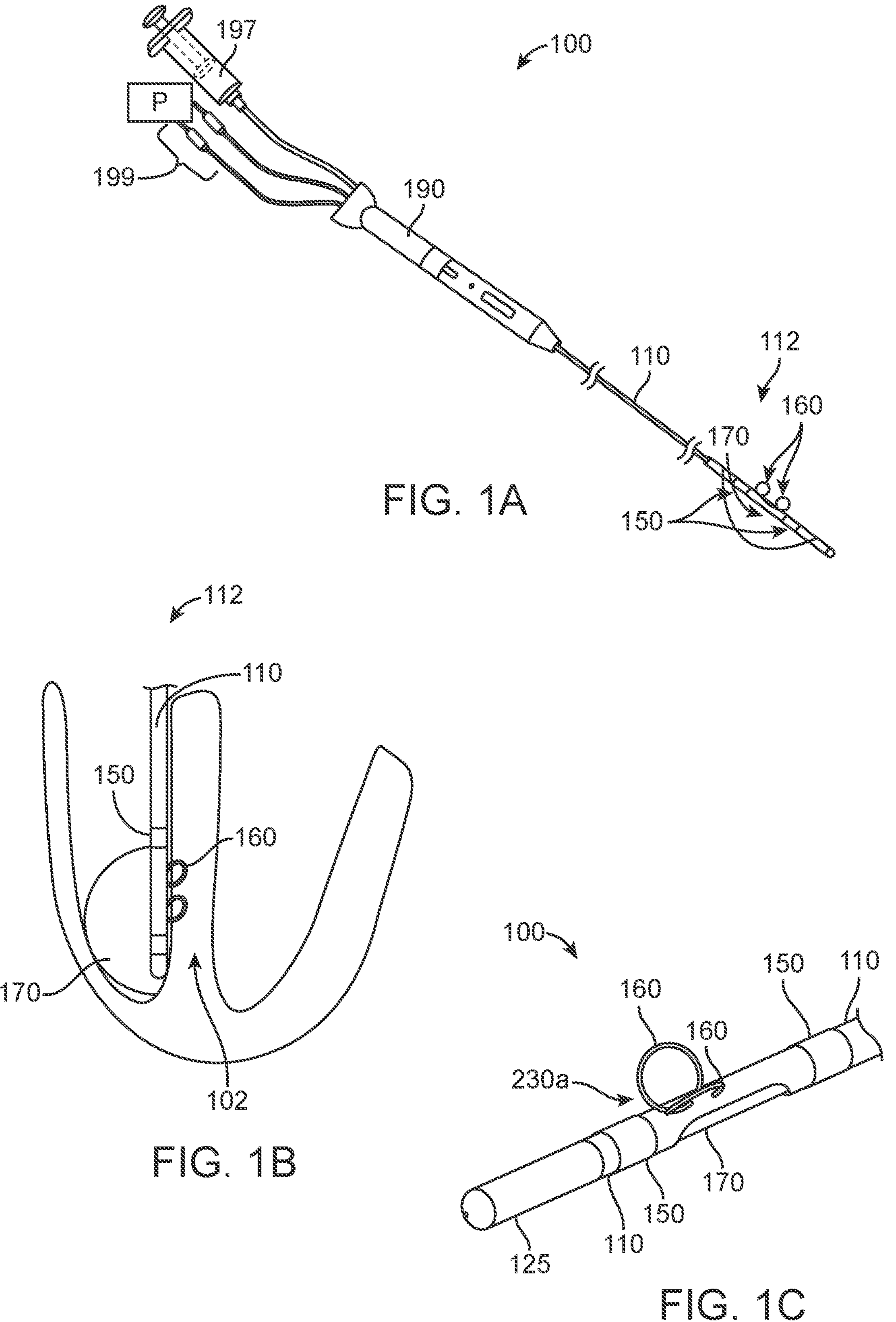
FIG. 1A shows a perspective view of a temporary pacing lead device, according to embodiments of the present disclosure.
FIG. 1B shows a section view of the temporary pacing lead device of FIG. 1A placed into a cardiac chamber of the heart of a subject, according to embodiments of the present disclosure.
FIG. 1C shows a perspective view of the working distal portion of the temporary pacing lead device of FIGS. 1A and 1B, according to embodiments of the present disclosure.

FIG. 1A shows an exemplary temporary pacing lead device 100 which may include one or more of: an elongate lead body 110 having a distal portion 112; an electrode array 150 coupled to the distal portion of the elongate lead body; an anchoring element 160 disposed within the elongate lead body and having a distal anchor tip, in which the anchoring element 160 is selectively operable in a first configuration in which the anchor tip is substantially retracted within the elongate lead body and in a second configuration in which the anchor tip is at least partially extended outside the elongate lead body and configured to fixate within the tissue 102; and optionally a displacement mechanism 170, coupled to the distal portion 112 of the elongate lead body 110, that is selectively expandable to bias the electrode array 150 and/or the anchoring element 160 toward the tissue 102. In some embodiments, instead of or in combination with one or more of the anchoring elements 160 fixating with the tissue 102, one or more of the anchoring elements 160 may simply contact and push against the tissue 102 to stabilize the temporary pacing lead device 100 at the target implantation region. In some embodiments, the one or more of the anchoring elements 160 may have a screw, a screw-like structure, a barb, a barb-like structure, or the like at its tip to facilitate fixation within the tissue 102. The device 100 may further include an actuator disposed within the lead body 110 and abuttingly engaged with or otherwise coupled to the anchoring element 160 to actuate the anchoring element 160 between the first and second configurations. The device 100 may further include a detachable handle 190 that is coupled to the elongate body 110. The detachable handle 190 may include a slide coupled to the actuator with first and second slide positions corresponding to the first and second configurations of the anchoring element, respectively. The detachable handle 190 and/or other handle may be a low-profile handle. In some embodiments, the anchoring element(s) 160 may serve as electrodes as an alternative to or in combination with electrode array 150. The proximal ends 199 of the electrodes of the device 100 may be coupled to an external power source P. The proximal ends 199 of the electrodes of the device 100 may be positioned proximal the detachable handle 190. The detachable handle 190 may also be coupled to a fluid pump 197 for the displacement mechanism and/or contrast fluid. The proximal end of the handle 190 may include ports that receive generator electrode plugs for the external generator P and/or fluid supply (e.g. Luer lock coupling) for the displacement mechanism 170 and/or contrast medium.

The device 100 may be used to securely place a pacing electrode lead in or against cardiac tissue, such as for temporary pacing and/or bradycardia support. The device 100 can enable reliable implantation and maintenance of the position of the electrode lead. In particular, as shown in FIG. 1B, the elongate body 110 is preferably navigable through the cardiovascular system (e.g., veins, arteries) into the right ventricle of the heart, such that when the displacement mechanism 170 is expanded, the electrode array 150 and/or one or more anchoring elements 160 are biased towards the intraventricular septum. The anchoring elements 160 are configured to fixate within and/or approximate against tissue to secure the electrode array in contact with the intraventricular septum (tissue 102), which the electrode array may stimulate to help regulate heart rate, for example, via unipolar, bipolar, and/or other pacing. However, the device may alternatively be used to secure any suitable electrode array in any suitable tissue. For instance, in one variation (e.g., including the electrode array, anchoring elements and a mode of delivery such as a catheter, without including a displacement mechanism), the device may be used in applications such as laparoscopic surgery, general surgery, spinal surgery, and/or other procedures for any suitable tissue. In another instance, the device 100 may be placed against the epicardium for epicardial stimulation. In some embodiments, customized implantation tools, for example, tissue tunneling instruments, may be provided to facilitate advancement and deployment of the device 100 to the various placement locations. While the device 100 is shown with anchoring elements 160 deployable from separate ports, the anchoring elements 160 may instead deploy from a common port 230a as shown in FIG. 1C. The anchoring elements 160 may deploy from the common port and diverge from another, for example, at an angle ranging from near 0 to 270 degrees, near 0 to 180 degrees, near 0 to 90 degrees, such as 45 degrees. The elongate body 110 may further comprise an atraumatic lead 125.

The temporary pacing lead device 100 may be placed at the target implantation site, for example, as a ventricular or epicardial lead, for any number of days, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 687, 68, 69, 70, 71, 72, 73, 74, 75, 76, 77, 78, 79, 80, 81, 82, 83, 84, 85, 86, 87, 88, 89, 90, or more days. Common device placement times may be for up to around 7 days, up to around 30 days, or up to around 180 days. One or more of the temporary pacing lead devices 100 may be implanted at any one time. In many embodiments, the temporary pacing lead device 100 may provide short-term pacing support as needed through an entire time course of patient care from in-hospital to out-of-hospital. For example, the temporary pacing lead device 100 may be temporarily implanted and used during a transcatheter aortic valve replacement (TAVR) procedure, a transcatheter mitral valve replacement (TMVR) procedure, or similar procedure and then left in the patient while the patient recovers in-hospital from the procedure, and the temporary pacing lead device(s) 100 may then be removed as the patient transitions out of the hospital or the temporary pacing lead may be left in place for use when the patient is not in the hospital. In some embodiments, the temporary pacing lead device(s) 100 may be coupled to a first type of pacing signal generator during the hospital procedure and then coupled to a second type of pacing signal generator after the procedure. The second type of pacing signal generator may be a smaller profile, less intrusive, and more patient-comfortable pacing device than the first type, for example, as described below with the miniature pacing signal generator 400 allowing use of the device outside of the hospital.

The elongate lead body 110 of the device can function to contain and deliver the electrode array 150, anchoring element 160, and displacement mechanism 170 to target tissue within the body. The elongate lead body is preferably a steerable lead or other elongate body, such as a catheter with a stylet, preformed curve, or other internal steering system. Such steering systems are known by one ordinarily skilled in the art, although the elongate body or lead may include any suitable steering system for navigating in the cardiovascular system or other portion of the body. The lead is preferably approximately cylindrical, but may alternatively be substantially flat or planar, or have any suitable cross-section. The lead is preferably flexible and made of a biocompatible material such as polyurethane or polyimide, although at least some portions may be rigid.

Further temporary pacing lead devices that are applicable to the embodiments of the present disclosure are described in the following patents and patent applications: U.S. patent application Ser. No. 13/219,874, now U.S. Pat. No. 9,855,421, U.S. patent application Ser. No. 14/708,792, now U.S. Pat. No. 9,844,663, U.S. patent application Ser. No. 15/691,187, now U.S. Pat. No. 10,124,162, U.S. patent application Ser. No. 16/148,357, U.S. patent application Ser. No. 14/707,246, now U.S. Pat. No. 9,872,981, U.S. patent application Ser. No. 15/844,367, now U.S. Pat. No. 10,232,170, and U.S. patent application Ser. No. 16/256,473, which are incorporated herein by reference. Temporary pacing lead devices that are applicable to the embodiments of the present disclosure are also available from BioTrace Medical, Inc. of Menlo Park, CA, such as the Tempo® Temporary Pacing Lead.

Figures 2A, 2B:
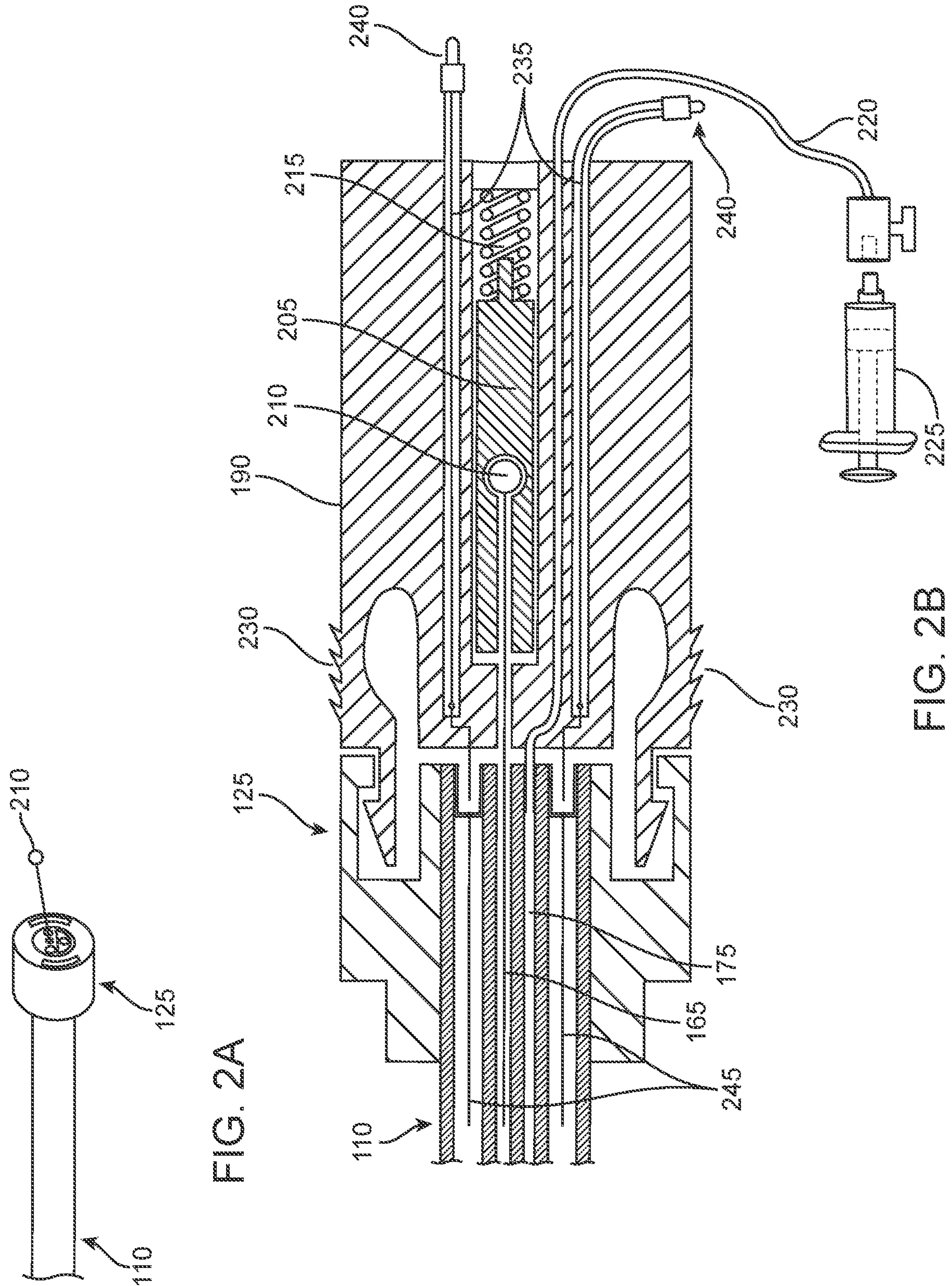
FIGS. 2A and 2B show a side view and a side section view of the proximal portion, respectively, of a temporary pacing lead device coupled to a detachable proximal handle attached, according to embodiments of the present disclosure.

FIGS. 2A and 2B show the proximal portion 125 of a temporary pacing lead device 100 coupled to an operation handle 190 used during the lead placement procedure described above. The operation handle 190 may comprise a shuttle 205 coupling to a stabilizer wire 165 of the temporary pacing lead device 100 that is coupled to the at least one anchoring mechanism 160, such as the ball tip 210 at the proximal end of the stabilizer wire 165 extended from the proximal end of the temporary pacing lead device 100. The ball tip 215 can be coupled to the shuttle 210 when the handle 200 is attached to the lead body 110; and the ball tip 210 can be decoupled from the shuttle 205 when the handle 190 is detached from the lead body 110. The operation handle 190 may further comprise a spring 215 to deploy the shuttle 205, and the shuttle 205 may be actuated to deploy the at least one anchoring mechanism 160. The operation handle 190 may further comprise a fluid inflation line 220, such as a balloon inflation line, to couple to a syringe or other fluid source 225 and the inflation lumen 175 of the temporary pacing lead 100 so that the syringe or other fluid source 225 may be operated to inflate or collapse the displacement member or inflatable balloon 170. The operation handle 190 may couple to the proximal end of the temporary pacing lead 125 with an airtight seal. The operation handle 190 may have one or more living hinges 230 pressable to release the operation handle 190 from the proximal portion 125 of the temporary pacing lead 100. The operation handle 190 may include conductive wires 235 and connectors 240 to the external generator P for pacing signals, for example, a pair of 2 mm pin connectors, a pair of 5 mm pin connectors, or a standard connector such as an international standard connector, for example, IS-1. The conductive wires 235 may be electrically coupled to conductive wires 245 in the temporary lead pacing device 100 which electrically connect to the distal electrodes.

Figures 3A, 3B:
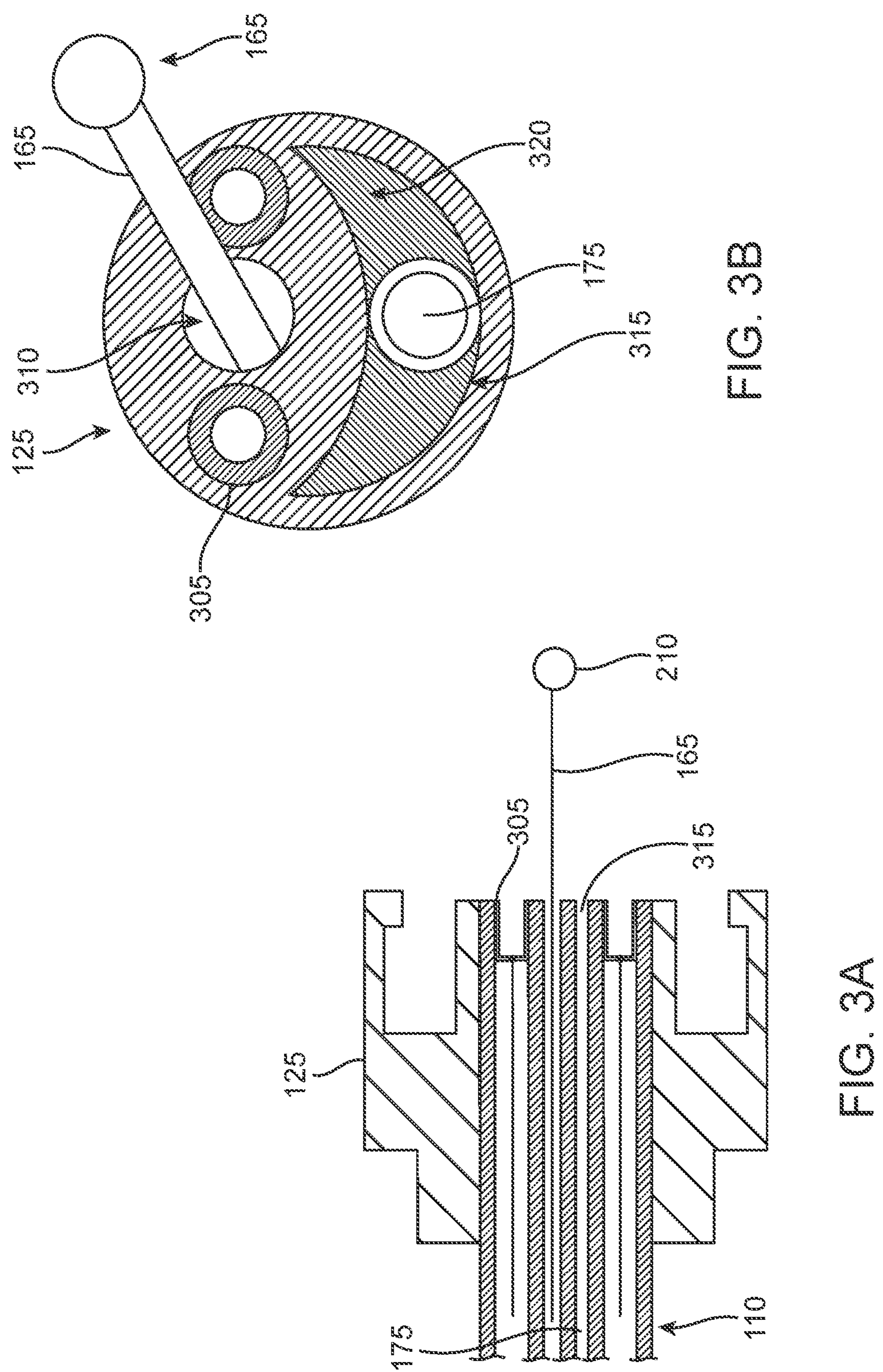
FIGS. 3A and 3B show a side section view and a cross-sectional view, respectively, of the proximal portion of a temporary pacing lead device, according to embodiments of the present disclosure.

FIGS. 3A and 3B show the proximal portion 125 of the temporary pacing lead device 100. As shown in FIG. 3A, the stabilizer wire 165 extends from the proximal end of the temporary pacing lead device 100 and should be protected to prevent inadvertent actuation of the at least one anchoring mechanism 160. As shown in cross section in FIG. 3B, the temporary pacing lead device 100 may comprise conductive tubing 305 to conduct pacing signals to the electrode array at the distal portion of the device 100, a lumen 310 for the stabilizer wire, and an inflation lumen 175 and inflation lumen port 315, typically surrounded by protective epoxy 320. In some embodiments, the displacement mechanism 170 is mechanically expanded such that the inflation lumen 175 and the inflation lumen port 315 are not required, but the device has an operational lumen for the displacement member 170. In other embodiments, the device 100 does not have a displacement member 170 and therefore any inflation lumen or inflation lumen port at all.

Figure 4:
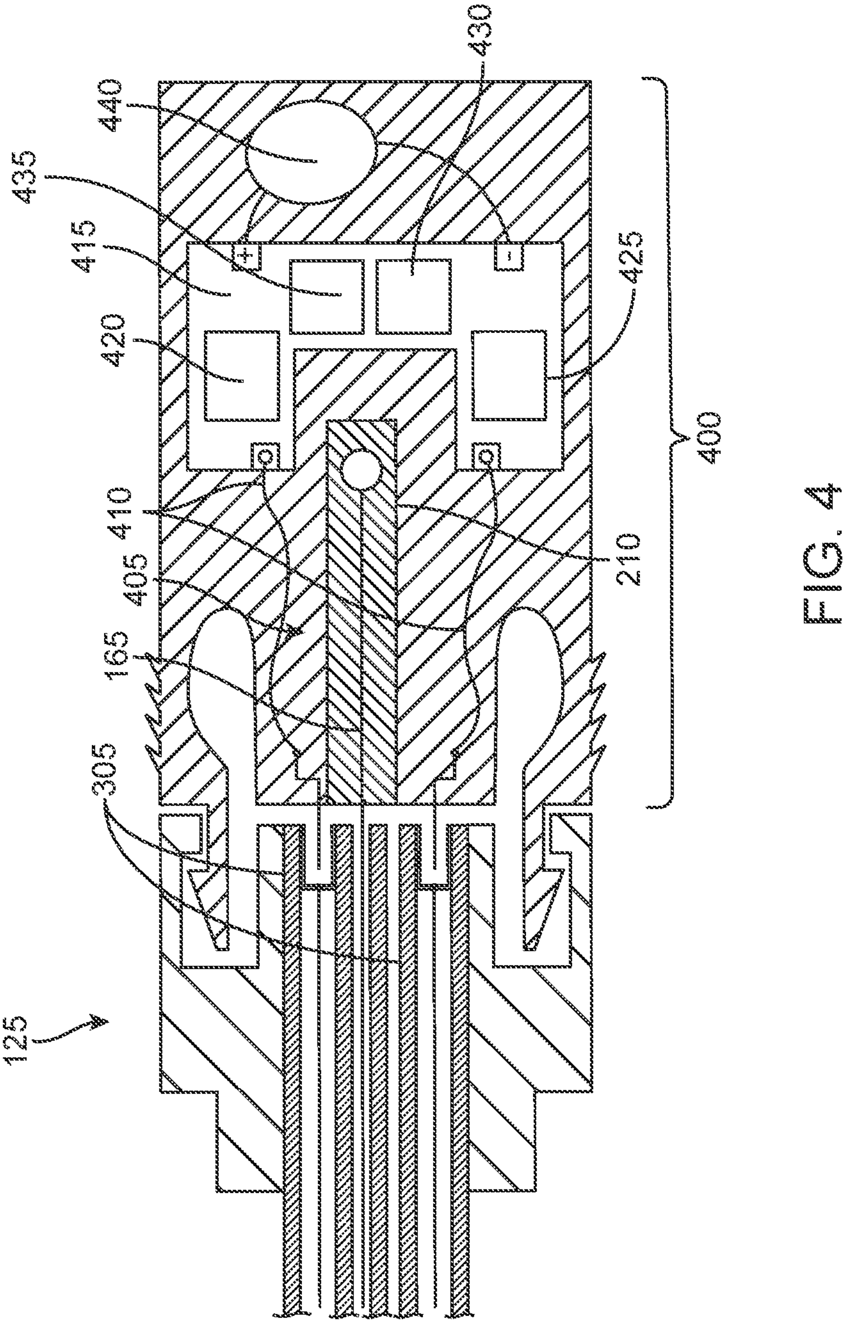
FIG. 4 shows a side section view of the proximal portion of a temporary pacing lead device coupled to a miniature pacing signal generator, according to embodiments of the present disclosure.

FIG. 4 shows the proximal portion 125 of the temporary pacing lead device 100 coupled to a miniature pacing signal generator 400. The miniature pacing signal generator 400 may have a protective slot 405 for the stabilizer wire 165 and its ball tip 210 extending proximally from the proximal end 125 of the temporary pacing lead device 100. The miniature pacing signal generator 400 may also comprise a plurality of electrodes 410 to couple to the conductive tubing 305 of the temporary pacing lead device 100 to provide pacing signals. The miniature pacing signal generator 400 may comprise a generator or processor 415 to generate the signal. The miniature pacing signal generator 400 may also comprise one or more of a signal recorder with a memory 420 (such as removable external memory), a wireless signal transmitter and/or receiver 425 (such as a BLE/MCU module), an RF antenna 430, analog circuitry 435 (such as resistors, capacitors, comparators, and amplifiers) for power management, and a power source 440, such as a primary cell battery, for example, a coin cell battery. In some embodiments, the miniature signal generator 400 includes one or more sensors to detect the presence of bodily fluid and tissue, for example, via changes in detected impedance from the electrodes at the distal end of the pacing device 100 electrically coupled to the miniature signal generator 400, and the miniature signal generator 400 may be configured to automatically start upon such detection. In some embodiments, the miniature signal generator 400 has the ability to read electrocardiogram (ECG) and/or detect clinically significant events in real-time and wirelessly communicate the detected ECG signals and/or clinically significant event(s) to a separate device, for example, via Bluetooth low energy (BLE) or other wireless transmission protocol.

Figure 5:
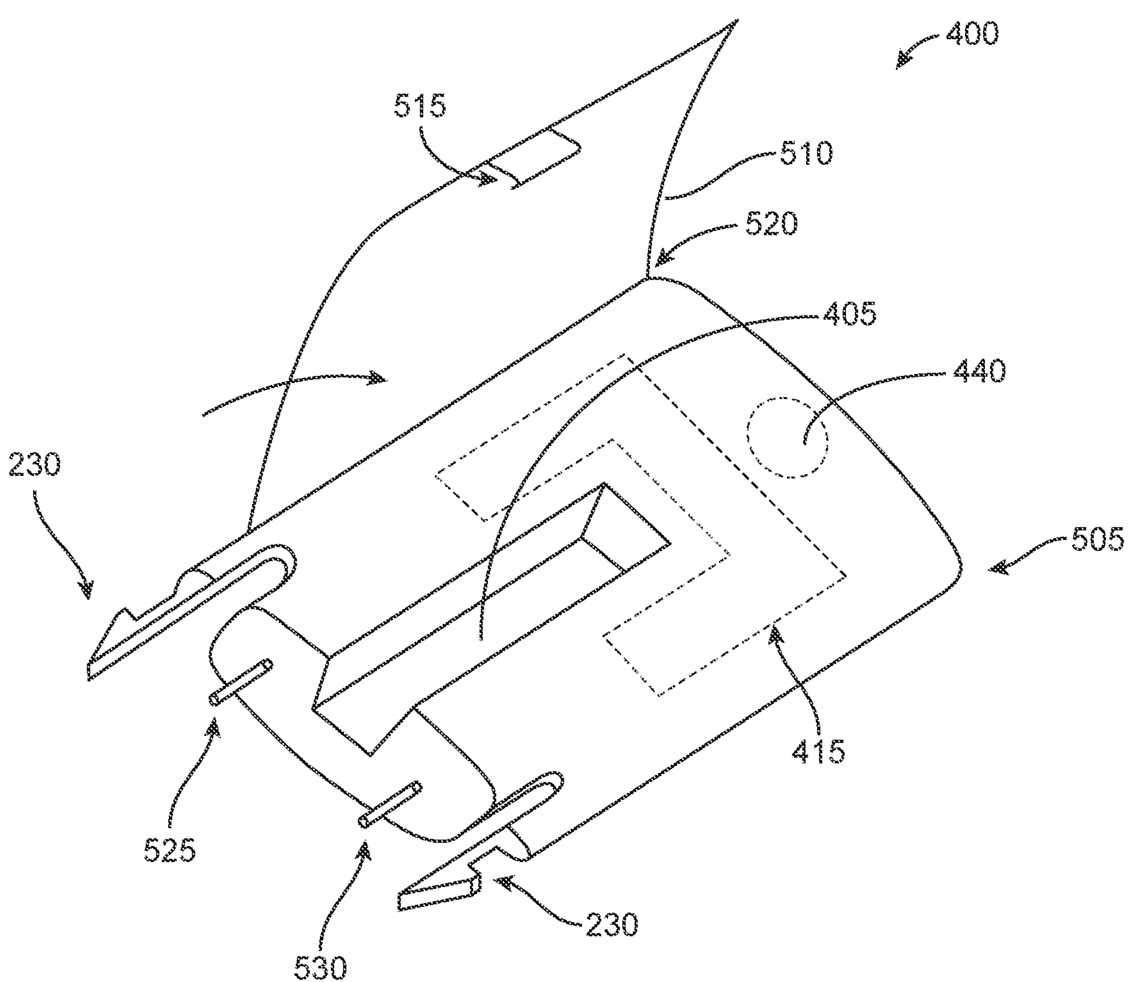
FIG. 5 shows a perspective view of a miniature pacing signal generator, according to embodiments of the present disclosure.

FIG. 5 shows a perspective view of the miniature pacing signal generator 400. The miniature pacing signal generator 400 may comprise a housing 505 and a lid 510 with a snap or other feature 515 to lock the lid 510 onto the housing 505. The miniature pacing signal generator 400 may have a hinge 520 for the lid 510 to rotate about, and the lid 510 may be rotated to access open parts of the housing 505, for example, to place or remove the primary battery or power source 440 and/or position the stabilizer wire 165 and its ball tip 210 within the protective slot or pocket 405. The signal generator or processor 415, in the form of a printed circuit board, for example, may be held internally by the housing 505. A cathode connector pin 525 and an anode connector pin 530 may extend from the housing 505 to couple to the conductive tubings 305 of the temporary pacing lead device 100. The pins 525, 530 may be in the form of pogo pins. The miniature pacing signal generator 400 may further comprise attachment mechanisms, such as living hinge attachment mechanisms 230, to detachably couple to the proximal end of the temporary pacing lead device 100.

Figure 6:
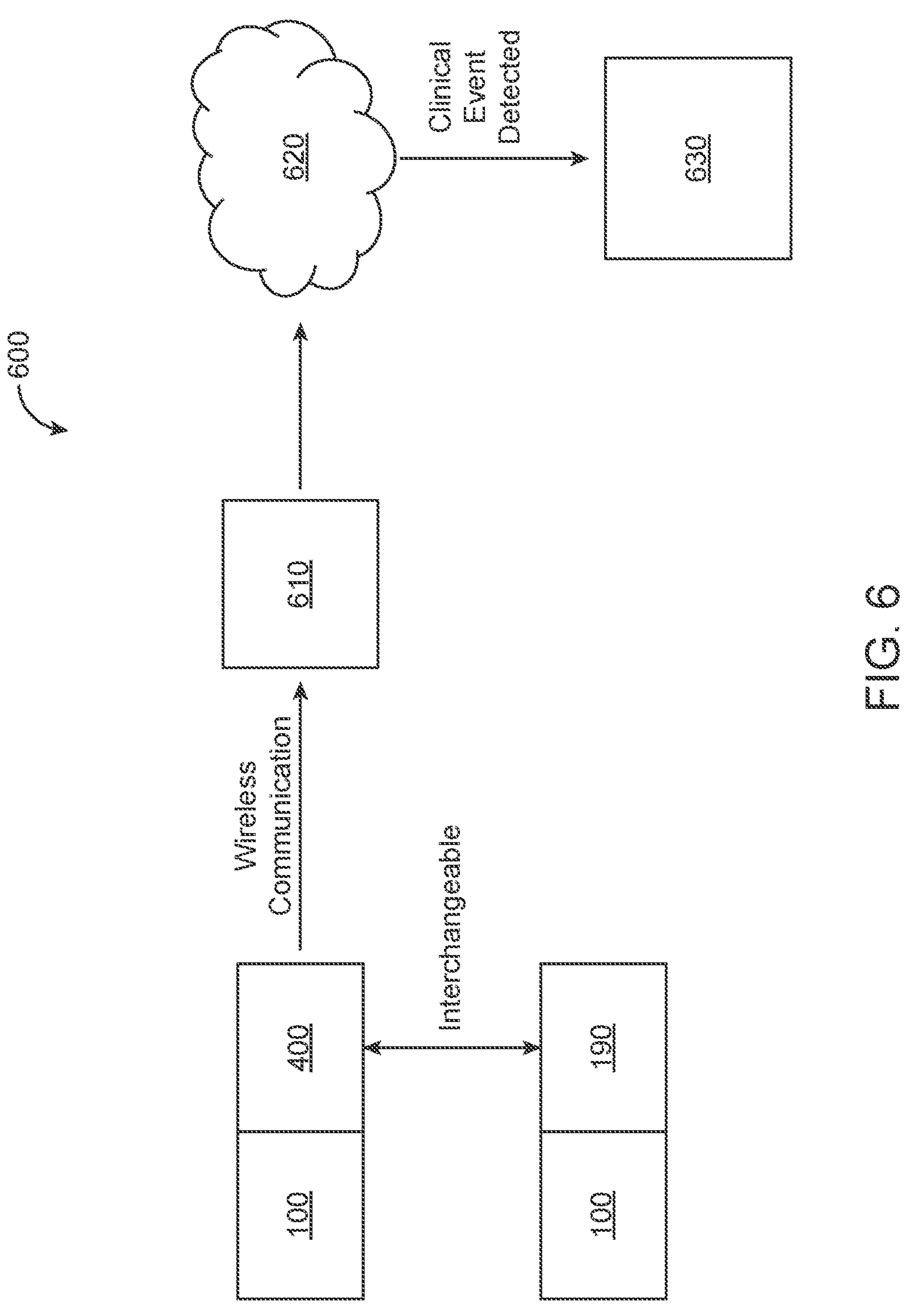
FIG. 6 shows a schematic of an exemplary use case of a miniature pacing signal generator coupled to a temporary pacing lead device, according to embodiments of the present disclosure.

FIG. 6 shows a diagram or schematic of an exemplary use case 600 of the miniature pacing signal generator 400 coupled to the temporary pacing lead device 100. The temporary pacing lead device 100 may interchangeable couple to the miniature pacing signal generator 400 or the control handle 190. The miniature pacing signal generator may wirelessly communicate with a computing device 610 of the subject and/or the supervising medical professional. These computing devices 610 include but are not limited to smartphones and tablet computers. The computing devices 610 may upload recorded signals to a remote server 620 (e.g., the cloud) and in the event of detection of a clinical event, the supervising or other medical professional may be alerted in real-time 630. Such an alert 630 may be useful in cases where the subject has left the hospital and/or clinic after a procedure and before the subject has returned for removal of the temporary pacing lead device.

Figure 7A:
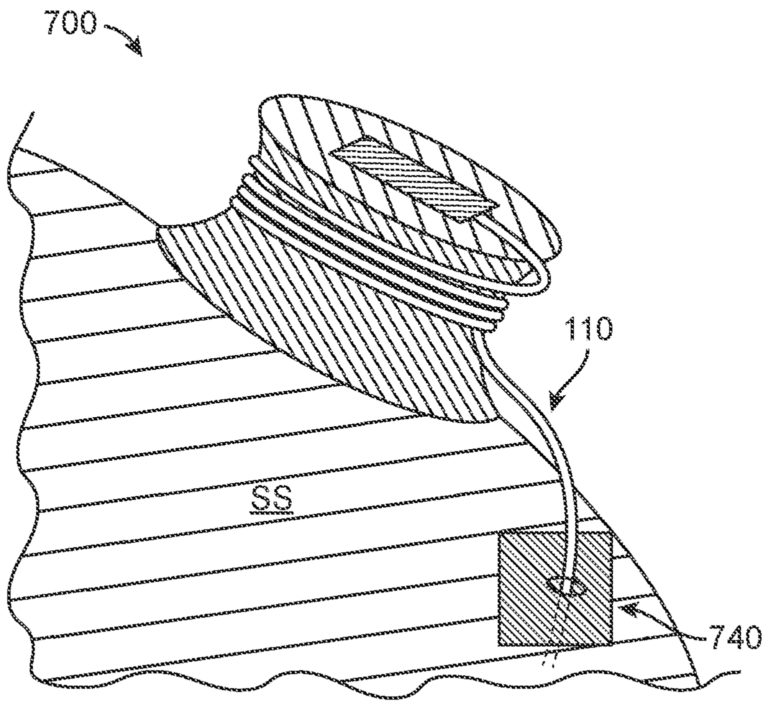
FIGS. 7A and 7B show a perspective view and a side view, respectively, of a retention patch for a miniature pacing signal generator coupled to a temporary pacing lead device, according to embodiments of the present disclosure.
Figure 7B:
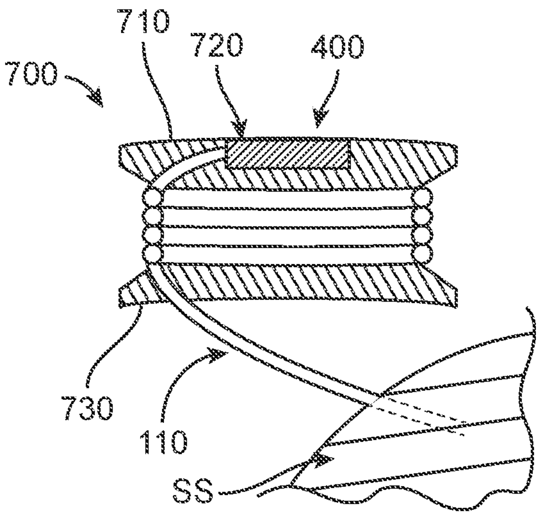

The temporary pacing lead device 100 often extends externally from the body of the subject at the access site (e.g., a femoral vein, a jugular vein, subclavian vein, or other access site), and the miniature pacing lead device 400 may couple to the temporary pacing lead device 100 externally of the body. Embodiments of the present disclosure also provide retention devices to hold the external portion of the temporary pacing lead device 400 and the miniature pacing lead device 100 in a low-profile, safe, and unobstructive manner. As shown in FIGS. 7A and 7B, the retention device 700 may comprise a spindle-like patch over or other wrapping feature 710 which a portion of the lead body 110 may be wrapped and having a pocket or slot 720 to accommodate the miniature pacing signal generator 400. The patch, for instance, its bottom surface 730, may be mounted on a skin surface SS. An adhesive dressing 740 may further be provided at the access or insertion site to prevent infection.

Referring back to the control handle 190, FIG. 8A shows a side view of a proximal portion of a temporary pacing lead device 100 with the detachable proximal handle 190 attached. FIG. 8B shows a side view of the proximal portion 125 of the temporary pacing lead device 100 with the detachable proximal handle detached. FIG. 8C shows a cross-section of the proximal end 125 of the temporary pacing lead device 100. FIG. 8D shows a cut-away side view of the detached detachable proximal handle 190, which may comprise cathode and anode connector pins. FIGS. 8E and 8F shows side views of the proximal portion 125 of the temporary pacing lead device 100 with the detachable proximal handle detached and the miniature pacing signal generator 400 attached. The miniature pacing signal generator may have a cylindrical form factor (FIG. 8E) or a flattened and rounded form factor (FIG. 8F).

Referring back to the retention devices and elements, a retention device or element may be in the form of a band or wrap 900. FIG. 9A shows a subject SB with the implanted temporary pacing lead device 100 with its proximal portion extending from the subject's body at a axillary, subclavian, femoral, or jugular vein access site or other acceptable insertion site 910 and retained on the subject SB with a retention band 900 on the arm AR. FIG. 9B shows a subject SB with the implanted temporary pacing lead device 100 with its proximal portion extending from the subject's body at a femoral vein access 920 and retained on the subject SB with a retention band 900 on the leg LG. In some embodiments as shown in FIG. 9C, the portion of the lead body 110 extending from the body may be lengthy and so a wire management element 930 may be provided for the external portion of the lead body 110 to wrap around. The wire management element 930 may comprise collars, for example Teflon, PTFE, or other non-stick collars, to retain the wrapped lead body.

Figure 10:
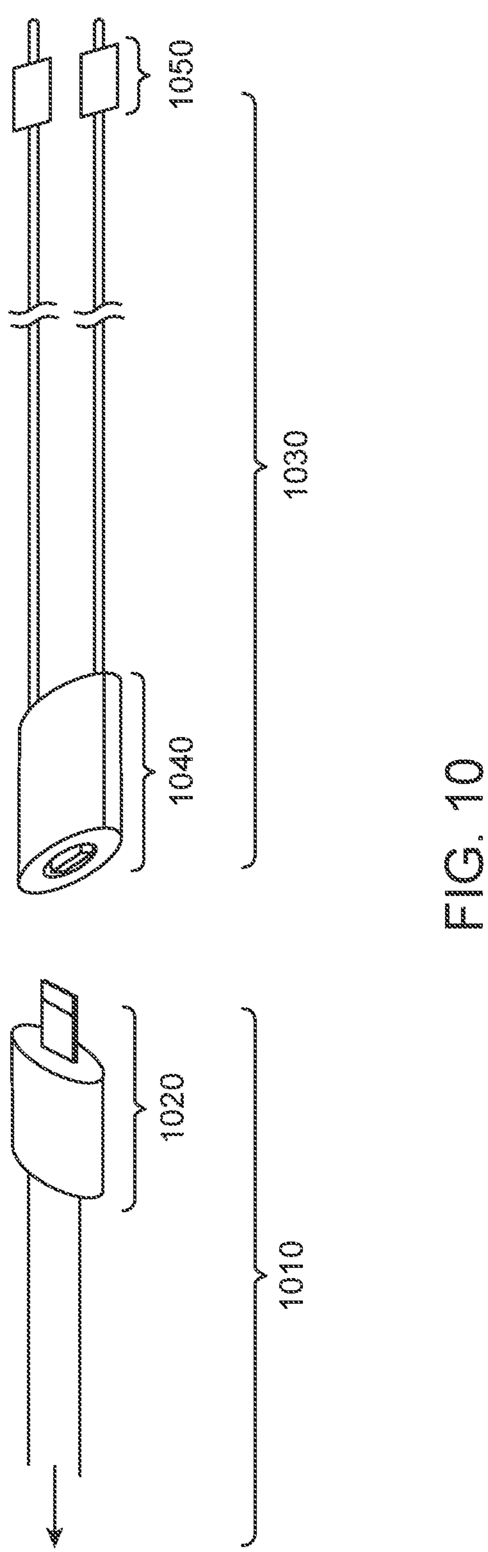
FIG. 10 shows a side view of a proximal portion of a temporary pacing lead device with a USB adapter and a detachable pacing signal generator connector pin adapter on the proximal end with a complementary USB adapter on the distal end, according to embodiments of the present disclosure.
Figure 11:
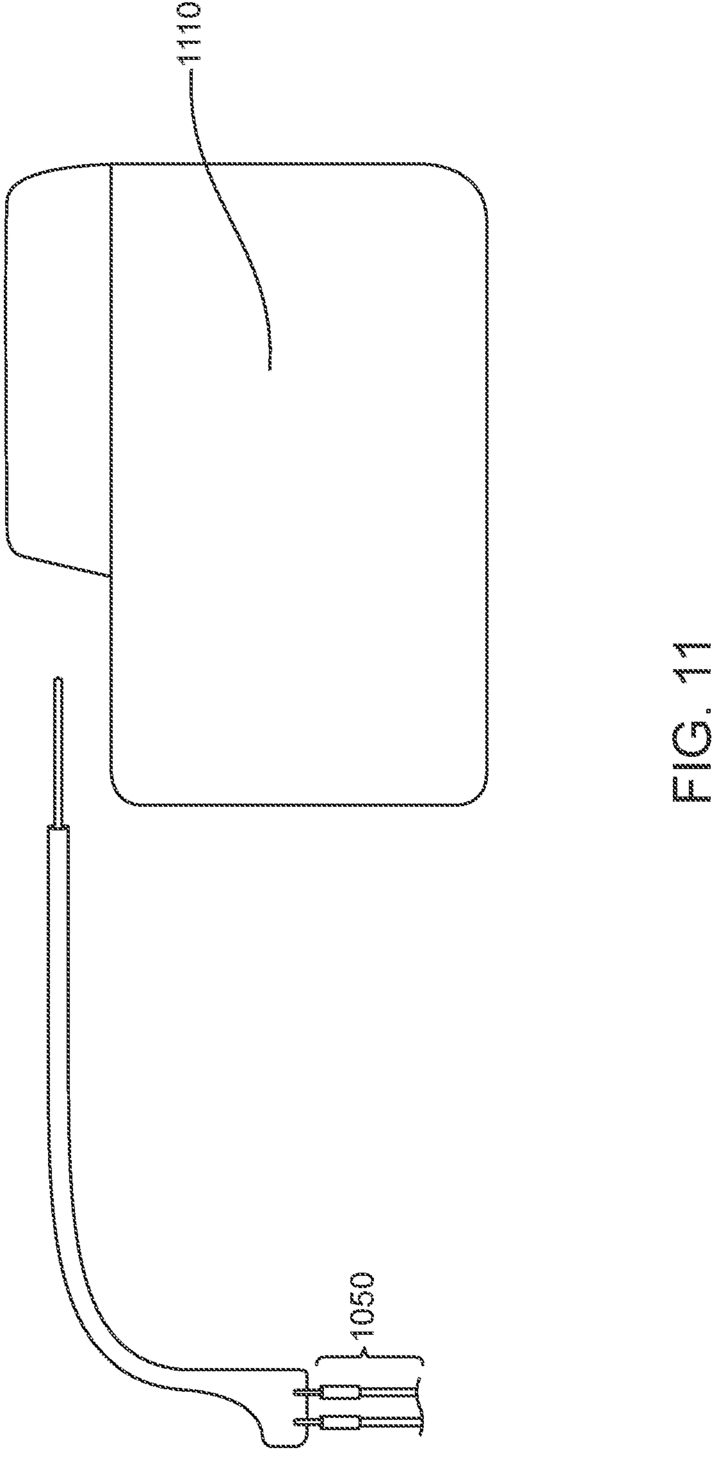
FIG. 11 shows a schematic of a proximal portion of a temporary pacing lead device couplable to a permanent pacing device, according to embodiments of the present disclosure.

In some embodiments, the miniature pacing signal generator 400 may connect with standard interface 1010, such as a USB interface, for example, a male micro-USB interface 1020, as shown in FIG. 10. The male micro-USB interface 1020 may couple to a detachable interface device 1030 with a complementary female micro-USB interface 1040. The detachable interface device 1030 may couple to an external signal generator 1110, such as a standard pacemaker, as shown in FIG. 11, with standard connector pins 1050 such as 2.0 mm connectors, 5.0 mm connectors, or IS-1 connectors.

Figure 12A:
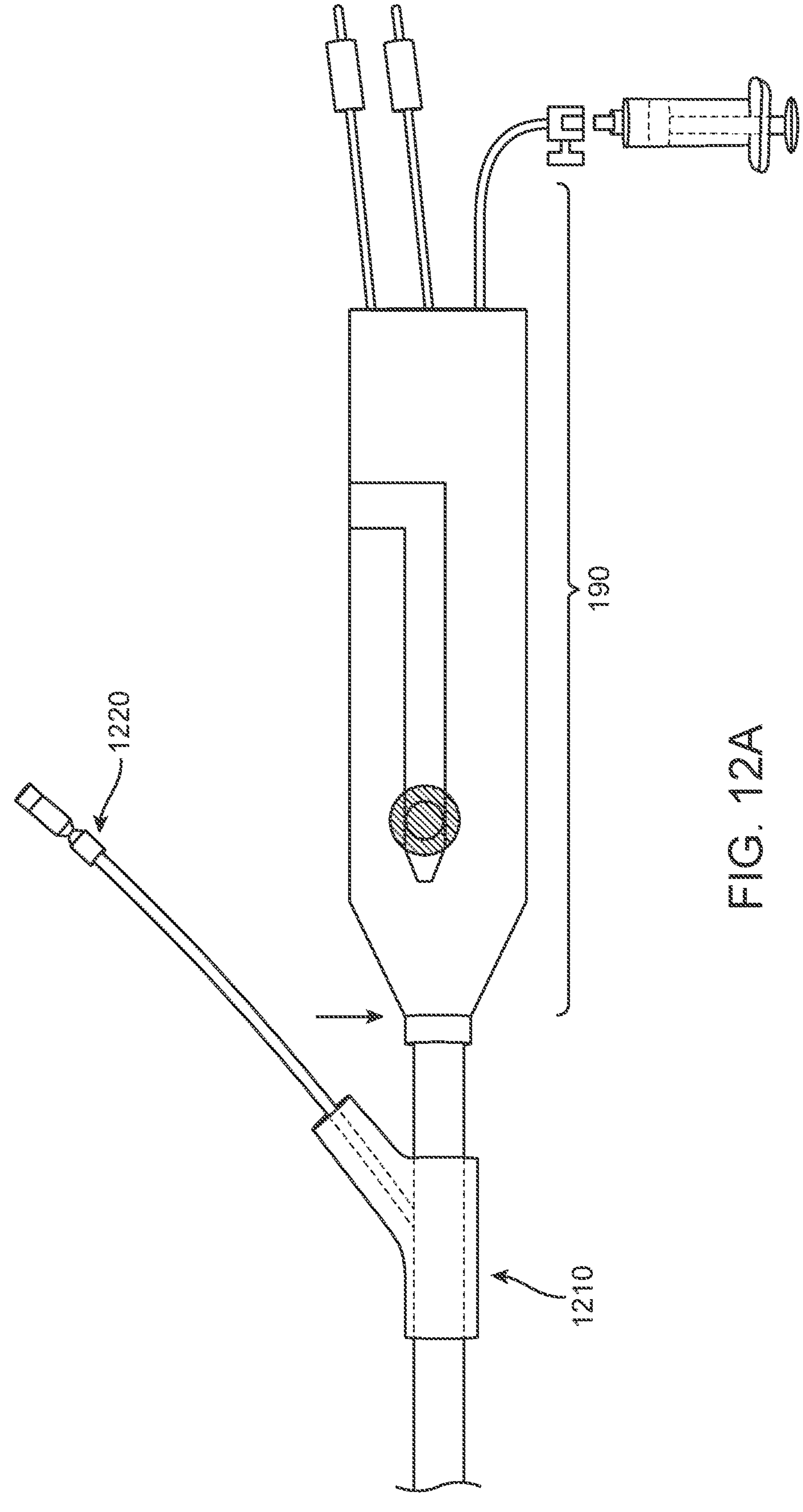
FIGS. 12A, 12B, and 12C show a side views of proximal portions of temporary pacing lead devices couplable to multiple devices, including a detachable control handle and a different pacing signal generating device, according to embodiments of the present disclosure.
Figures 12B, 12C:
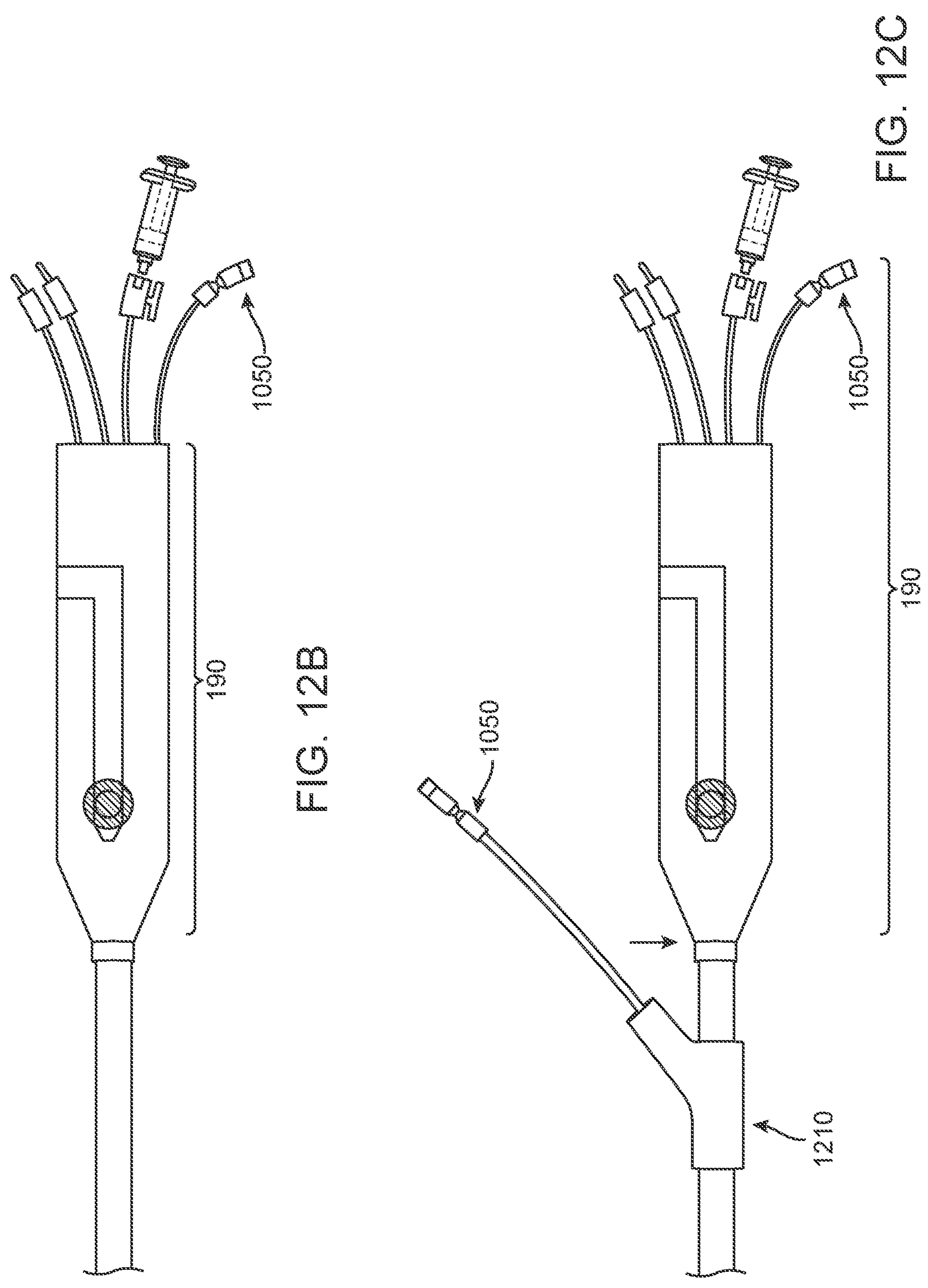

In some embodiments, a Y-connector 1210 may be provided as an intermediary between the detachable control handle 190 and a standard connector 1050 to a standard pacemaker device, for example, an IS-1 connector, as shown in FIG. 12A. In some embodiments, the detachable control handle 190 may comprise the standard connector 1050, and the detachable control handle 190 may be used alone as shown in FIG. 12B or with the Y-connector 1210 as in FIG. 12C.

FIG. 13A shows a cardiac chamber of a heart HT of a patient or a subject with a temporary pacing lead device 100 implanted therein. FIG. 13B shows a chest CH of the patient or subject, including the temporary pacing lead device 100 with its distal working portion implanted in the cardiac chamber of the heart HT and its proximal control portion extending out from the heart and vasculature and positioned near the neck access or insertion site 1310. FIGS. 13C, 13D, and 13E shows bottom, top, and side views of a retention patch 1320 for the proximal control portion of the temporary pacing lead device 100 extending from a subject's body. The retention patch 1320 may further comprise an adapter 1330 for a standard interface 1050 such as an IS-1 connector. The retention patch 1320 may further comprise an infection seal rim 1340. The retention patch 1320 may include a slot for the miniature pacing signal generator 400.

FIGS. 13F and 13G show an adapter at the proximal control portion of the temporary pacing lead device 100. This adapter 1360 may include a standard connector 1050 (such as an international standard connector interface, for example, IS-1) as well as anode and cathode pins for other signal generators, for example 2.0 mm pin connectors. The adapter may comprise a switch relay 1380 which can be toggled to switch between conducting pacing signals from the standard connector and the other connector pins.

Figure 13H:
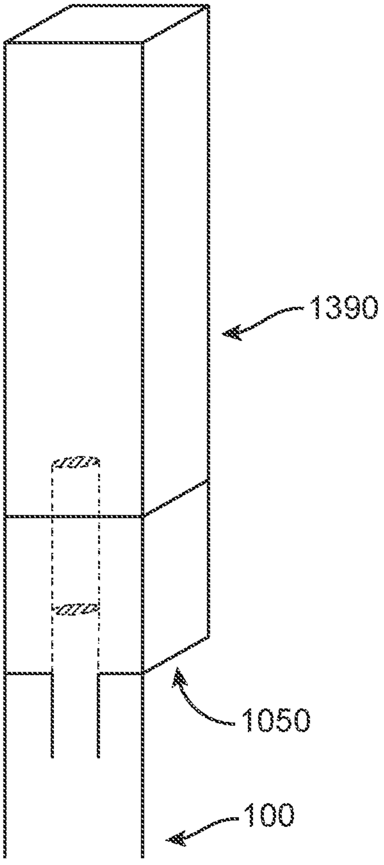
FIG. 13H shows a side section view of a subcutaneous retention device for coupling to an interface at a proximal end of the temporary pacing lead device, according to embodiments of the present disclosure.

In some embodiments, the proximal portion of the temporary pacing lead device 100 may extend from the heart through the vasculature near the access or insertion site but may not fully extend out of the body. In these cases, the signal generator and its power source may be subcutaneous as well. As shown in FIG. 13H, a small injectable battery 1390 may be injected subcutaneously to power the temporary pacing lead device 100, and a subcutaneous standard connector 1050 (such as an international standard connector interface, for example, IS-1) may be provided to couple the temporary pacing lead device 100 to a signal generator and/or power source.

Figure 14A:
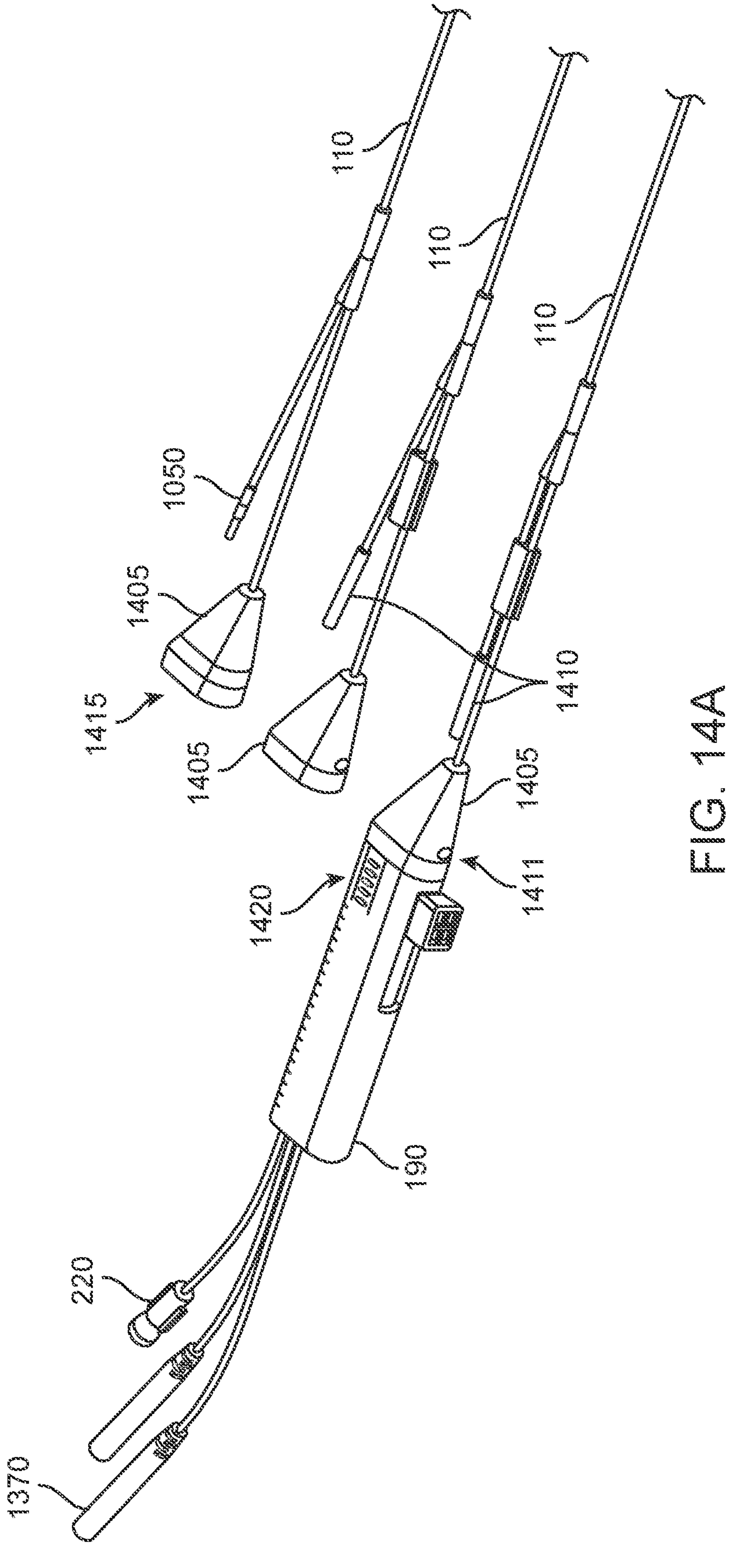
FIGS. 14A, 14B, and 14C show lead bodies of temporary pacing devices, according to embodiments of the present disclosure; 14A and 14B show perspective views of the lead bodies uncoupled to any attachment, coupled to a cap, coupled to a handle, or coupled to a miniature signal generator; and, FIG. 14C shows back and side views of the lead bodies with a non-detachable handle, a detachable handle, or a miniature pacing signal generator.
Figure 14B:
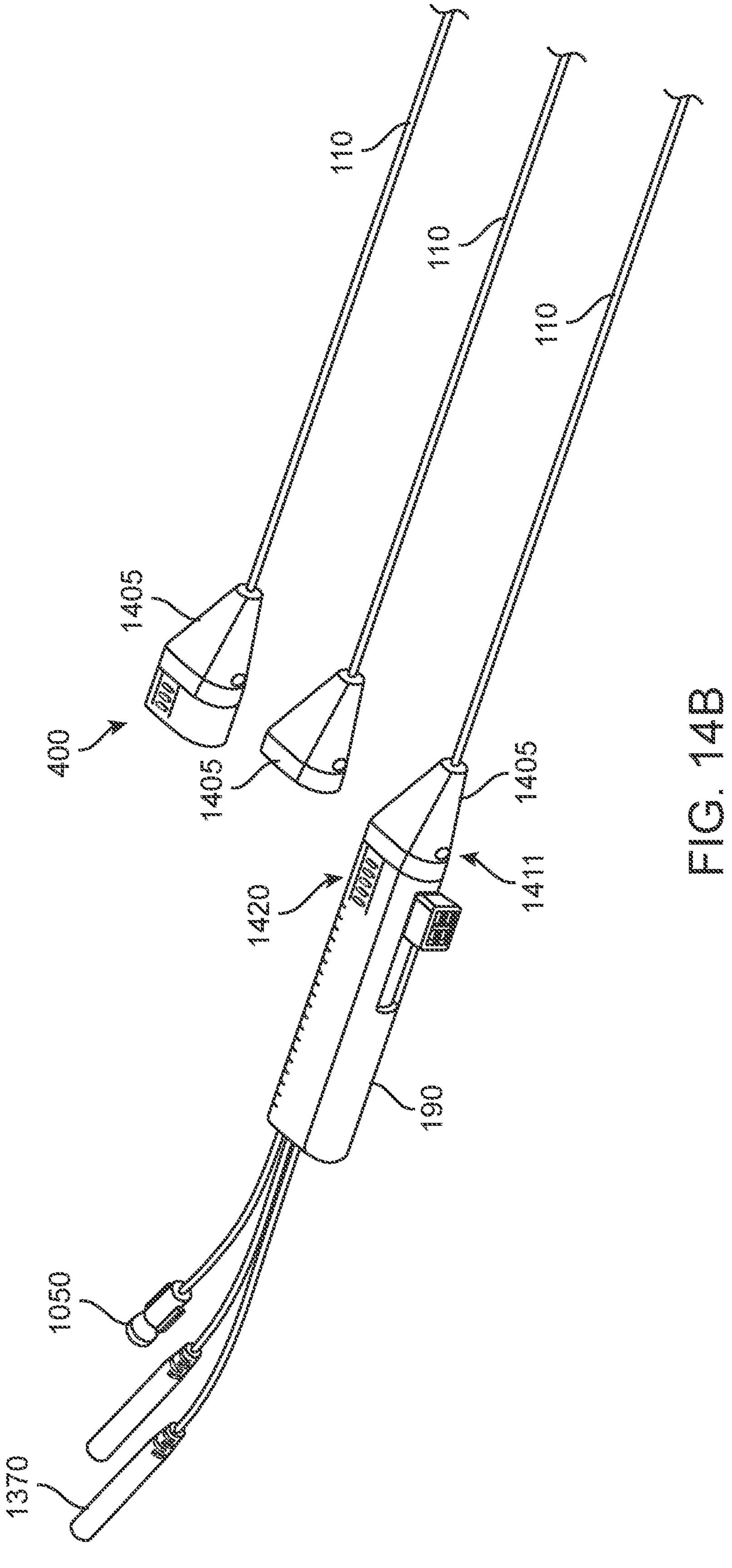
Figure 14C:
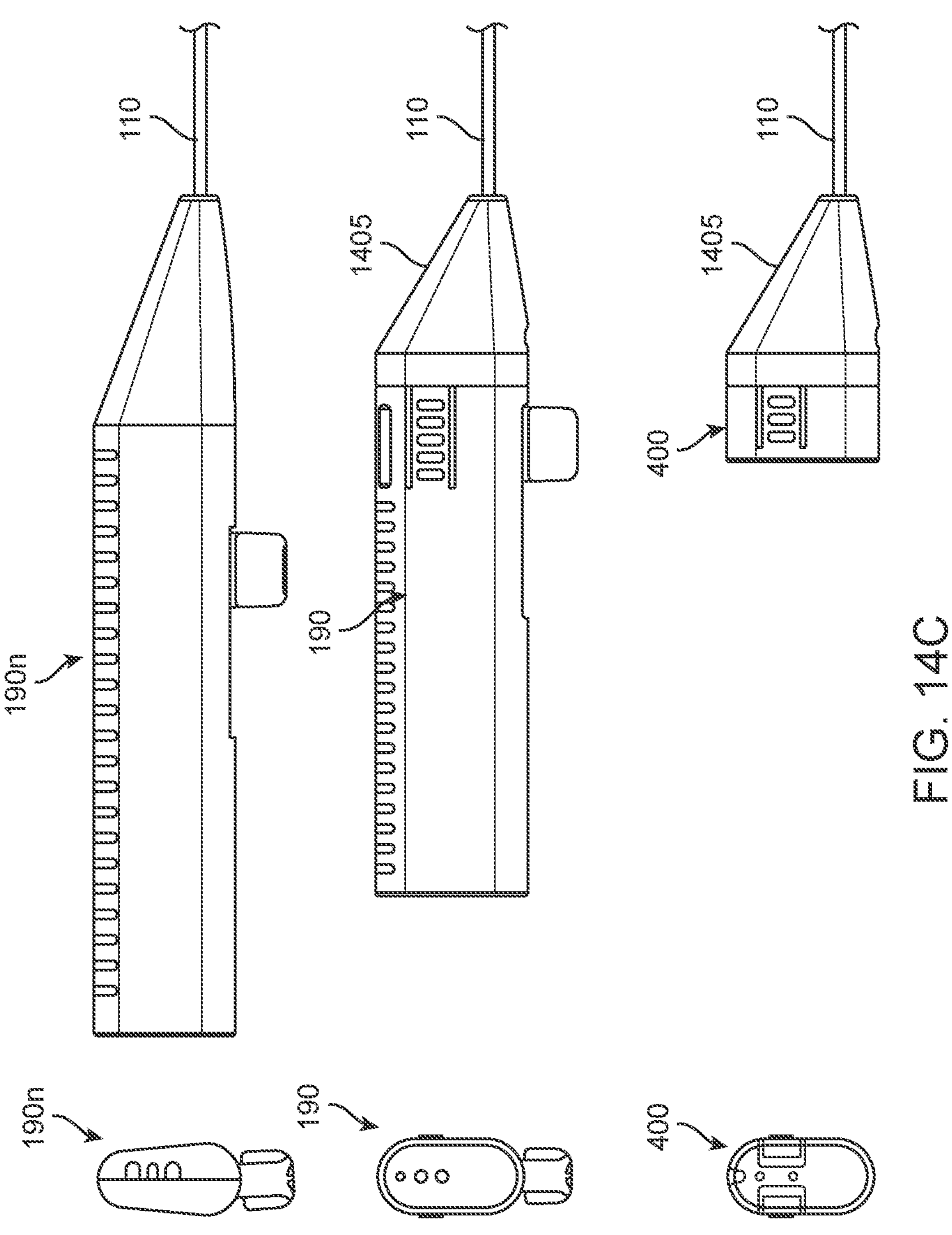

FIGS. 14A to 14C show the proximal portions of lead bodies 110 with a handle hub 1405 to couple the lead body to a variety of different components. The handle hub 1405 may be in the shape of a nose cone to conform to the handle 190. The handle hub 1405 may be fixedly attached to the proximal end of the lead body 110. The lead body 110 may be provided with a balloon inflation line 220 as shown in FIG. 14A or without as shown in FIG. 14B. In some embodiments, a cap 1410 for the standard connector 1050 may be provided. The handle hub 1405 may be provided with a cap 1415 as shown in FIG. 14A. The lead body 110 may be coupled to the handle 190 via the handle hub 1405. The handle 190 may have its own standard connector 1050 and anode and cathode pins 1370. The handle 190 may comprise a handle release lever 1420 to release the handle 190 from the handle hub 1410 of the lead body 110. The handle hub 1410 may comprise a locking and unlocking set screw 1411. As shown in FIGS. 14B and 14C, the lead body 110 may alternatively be coupled to a miniature signal generator 400. As shown in FIG. 14C, the lead body 110 may be coupled to a non-detachable handle 190*n*, the detachable handle 190 via the handle hub 1405, or a miniature pacing signal generator 400. While these three components may have similar cross-sectional profiles, for example, with a width of around 11-12 mm and a height of around 21-23 mm, the lengths of the non-detachable handle 190*n*, the detachable handle 190, and the miniature pacing signal generator 400 may vary between one another.

Figure 15A:
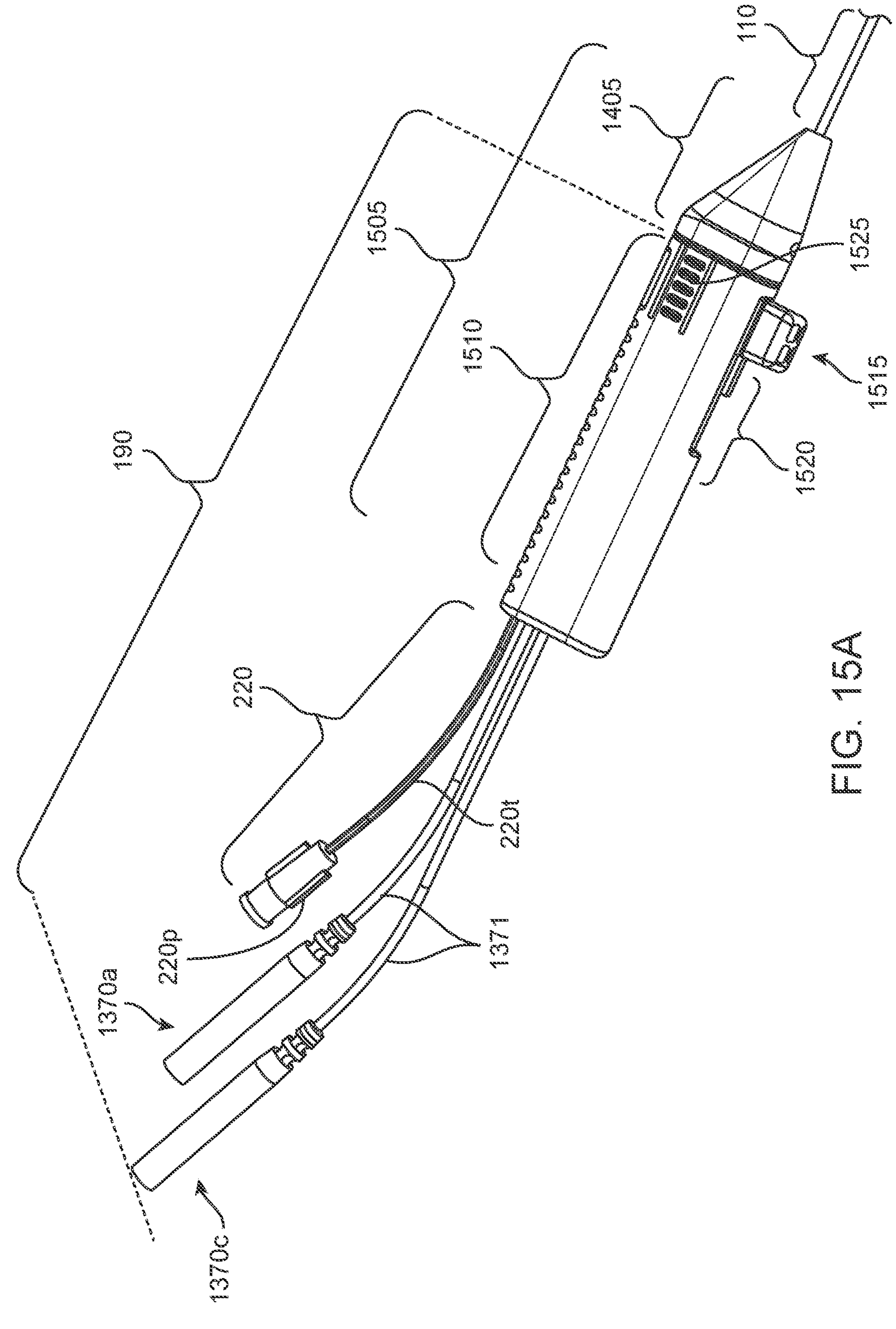
FIGS. 15A and 15B show a top view and an exploded top view, respectively, of a detachable handle coupled to a lead body of a temporary pacing device, according to embodiments of the present disclosure.
Figure 15B:
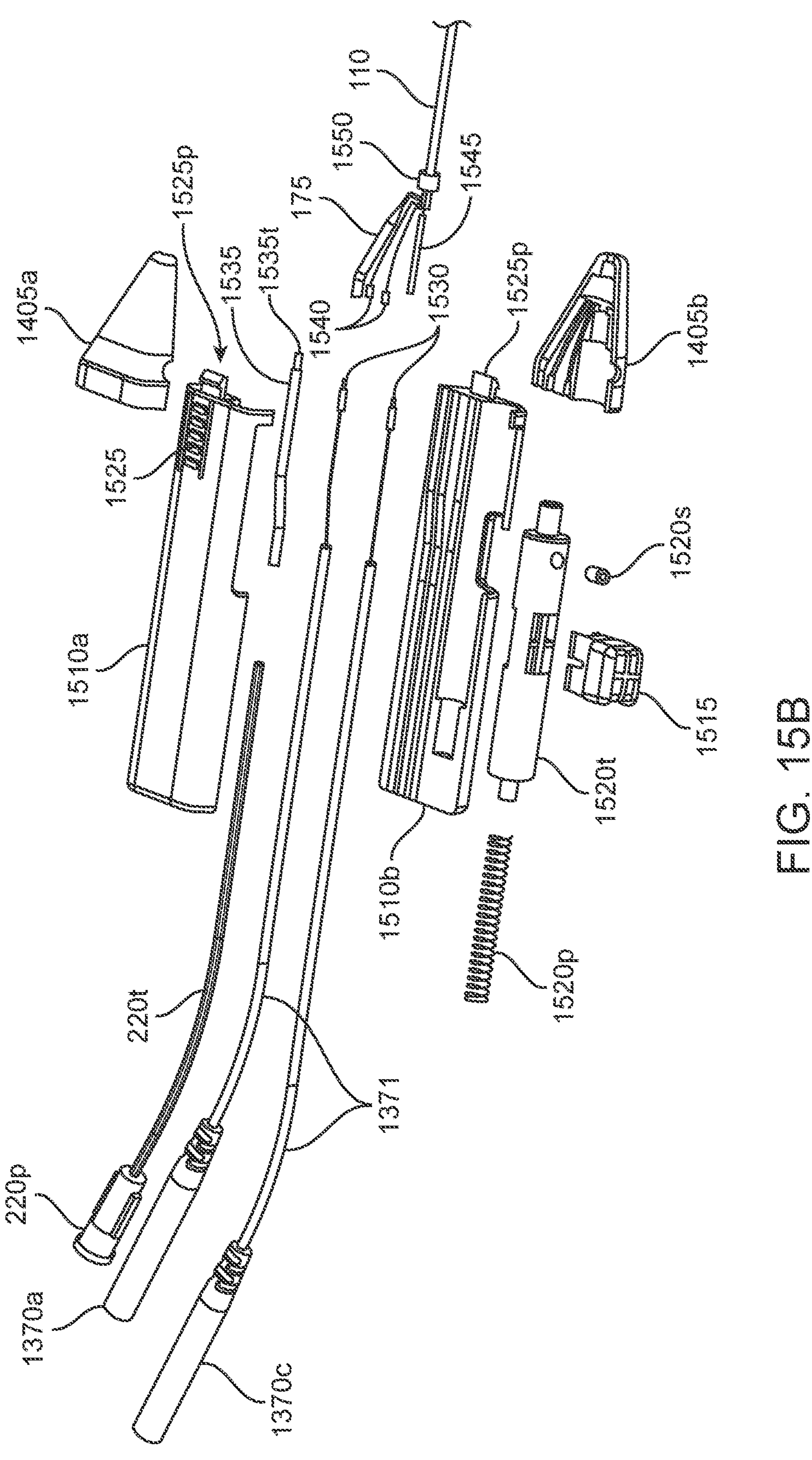

FIGS. 15A and 15B show the detachable handle 190 detachably coupled to the lead body 110 via the handle hub 1405. The handle portion 1510 may be formed by a top shell 1510*a* and a bottom shell 1510*b*. The handle portion 1510 of the detachable handle 190 may form a handle assembly 1505 with the handle hub 1405 which may be shaped as a nose cone. The handle hub 1405 may comprise a top shell 1405*a* and a bottom shell 1405*b*. The handle portion 1510 may comprise a deployment trigger 1515 slidable within a deployment trigger track 1520 to deploy the stabilizers and/or attachment mechanisms 160 of the temporary pacing device 100. The handle hub 1405 may comprise a stabilizer wire adapter 1545 to couple to the deployment trigger 1515. The deployment trigger track 1520 may comprise a shuttle 1520*t*, a spring 1520*p* coupled to the shuttle 1520*t*, and a set screw 1520*s*. The handle portion 1510 may comprise one or more connector tabs 1525 which may be pressed to detach the handle hub 1405 from the handle portion 1510. The connector tab(s) 1525 may comprise connector snap(s) 1525*p* to couple to complementary slot(s) in the handle hub 1405 and pressing the connector tab(s) 1525 may de-couple the snap(s) 1525*p* from the complementary slot(s). The handle 190 may further comprise a balloon inflation line 220 which may comprise a hollow tube 220*t* and an inflation port 220*p*. The balloon inflation line 220 may be coupled to the inflation lumen 175 of the lead body 110 via an inflation adapter 1535 with a tube adapter 1525*t*. The handle 190 may further comprise an anode or negative pin connector 1370*a* and a cathode or positive pin connector 1370*c*, each comprising insulated conductor wires 1371. These pin connectors may connect to an external generator and may be electrically conductive to the electrodes at the distal end of the lead body 110 that provide current and/or pacing signals to the tissue of interest, for example, via pogo pin connectors 1530 and conductor pads 1540 to the conductor wires within the lead body 110. The lead body 110 may comprise a collar 1550 to couple to the distal ends of the top shell 1405*a* and the bottom shell 1405*b*. The collar 1550 may limit proximal movement of the top shell 1405*a* and the bottom shell 1405*b* and may provide a leak-proof seal to prevent fluids from entering the handle hub 1405 and risking damage to the contents of the handle hub 1405.

FIGS. 16A to 16H show an exemplary method of operating the temporary pacing lead 100.

Figure 16A:
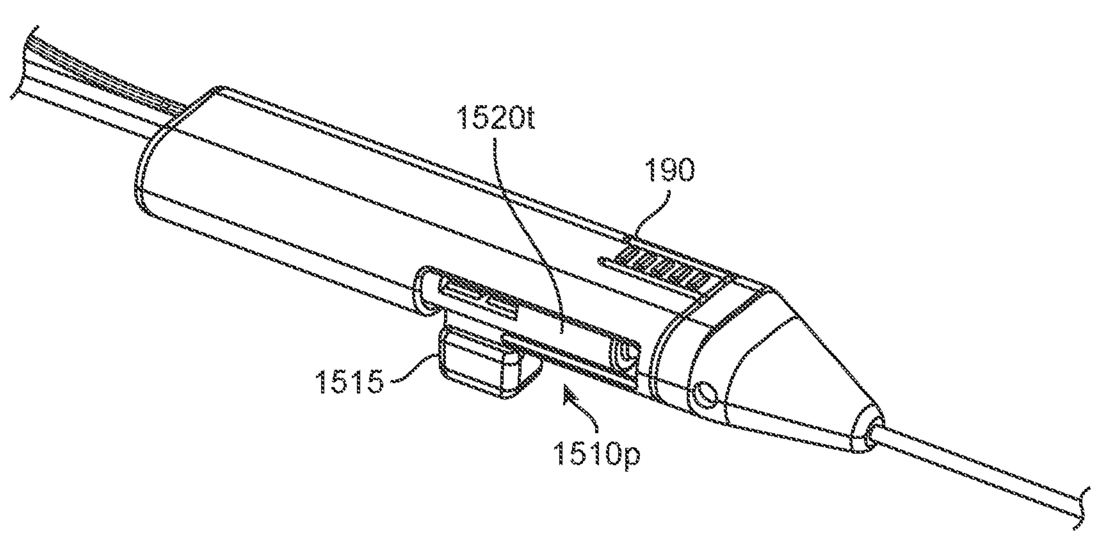
FIGS. 16A to 16H show an exemplary method of operating a temporary pacing device, according to embodiments of the present disclosure.

As shown in FIG. 16A, the deployment trigger 1515 may initially be in a retracted position, which may correspond to the stabilizer wire(s) and attachment mechanism 160 being in the retracted position and unexposed. The user can rotate the deployment trigger 1515 to deploy the stabilizer wire(s) and attachment mechanism 160. The deployment trigger 1515 may be coupled to the shuttle 1520*t*. The shuttle 1520*t* may be coupled to the spring 1520*p* that may be located proximal to the shuttle 1520*t*. The shuttle 1520*t* may not be free to translate or move because the deployment trigger 1515 may be constrained from translating forward or distally due to a handle shell feature or stop 1510*p*.

Figure 16B:
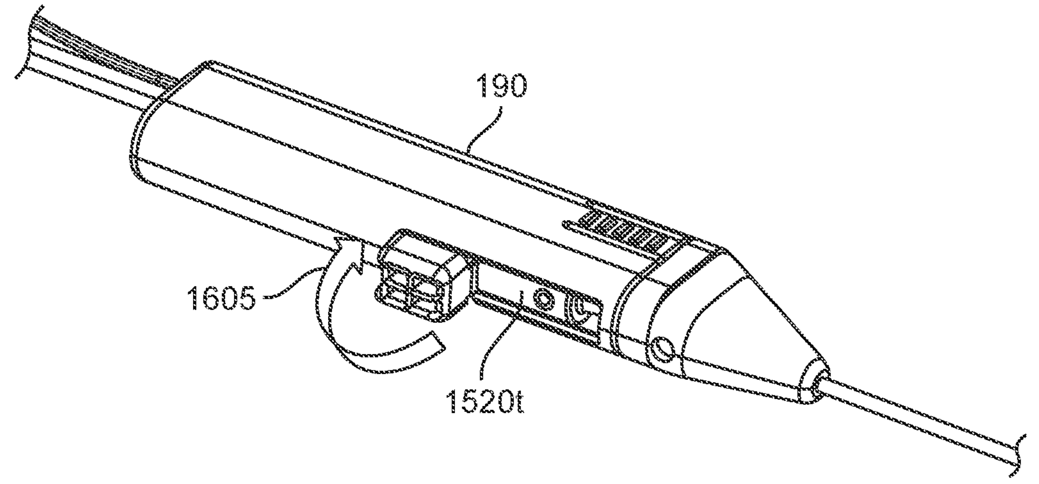

As shown in FIG. 16B, when the user rotates the deployment trigger 1515 as shown with arrow 1605, the spring 1520*p* which is in the compressed position can be free to expand. As the spring 1520*p* expands linearly, it can linearly translate the shuttle 1520*t* and thus linearly translate the stabilizer wires.

Figure 16C:
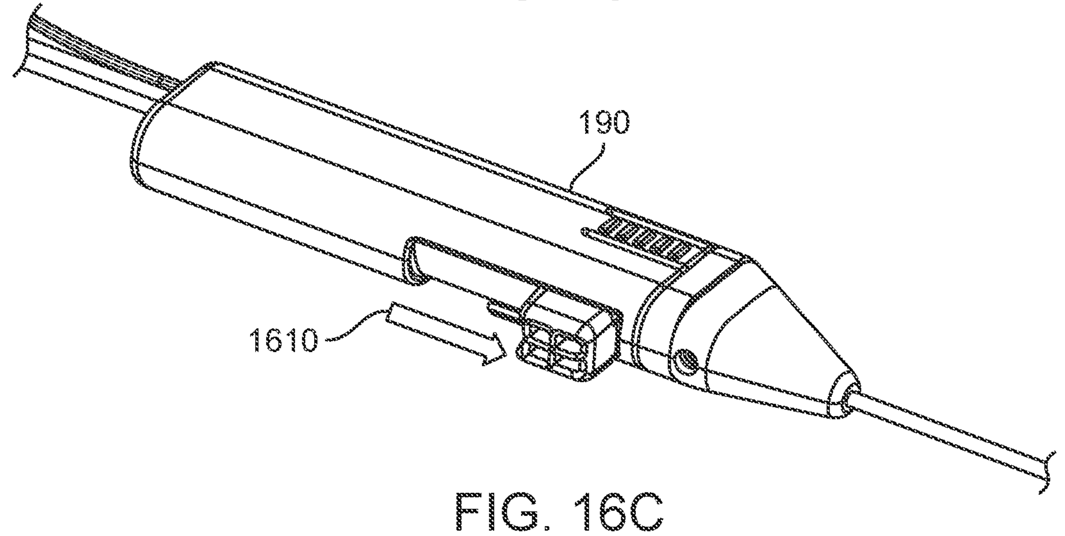

As shown in FIG. 16C, as the shuttle 1520*t* travels forward in a direction indicated by arrow 1610, the stabilizer wire may travel forward until the stabilizer wires on the distal end of the lead body are fully exposed. FIG. 16C shows the deployment trigger 1515 in the final position when the stabilizer wires are fully exposed.

Figures 16D, 16E, 16F:
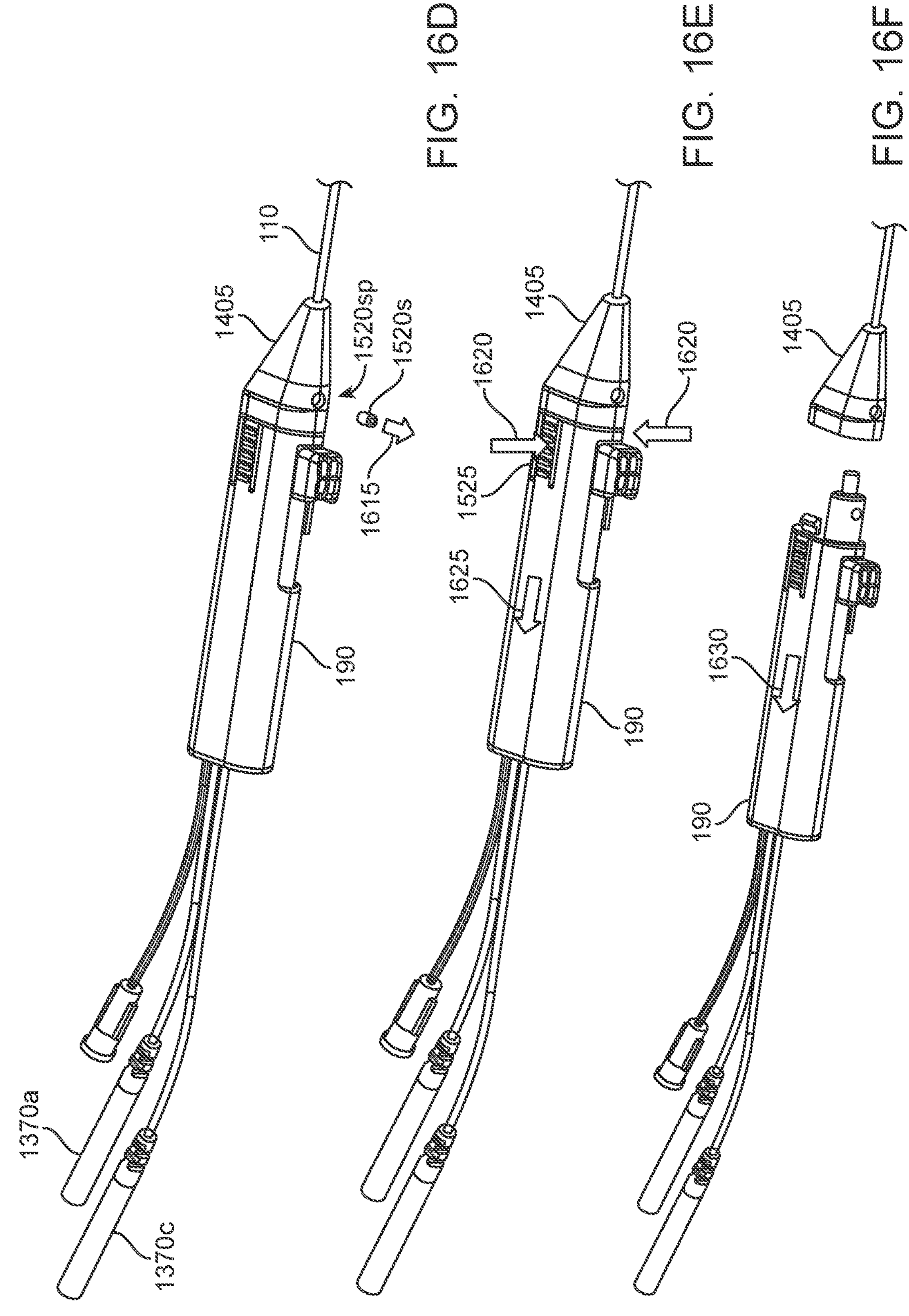

As shown in FIG. 16D, once the stabilizers are fully deployed, the user can connect the positive pin connector 1370*c* and the negative pin connector 1370*a* to an external generator. Once the user is done using the external generator, the user may disconnect the handle 190 from the lead body 110. The first step may be to remove the set screw 1520*s* via the set screw port 1520*sp* on the handle hub 1405 in the direction shown by arrow 1615.

As shown in FIG. 16E, to disengage the detachable handle 190 from the handle hub 1405, the user can simultaneously depress the connector tabs 1525 on both sides as indicated by arrows 1620.

As shown in FIG. 16F, once the detachable handle 190 is disengaged from the handle hub 1405, the detachable handle 1910 can be removed from the handle hub 1405 and the lead body 110, for example, by being retracted in a direction indicated by the arrow 1630.

Figure 16G:
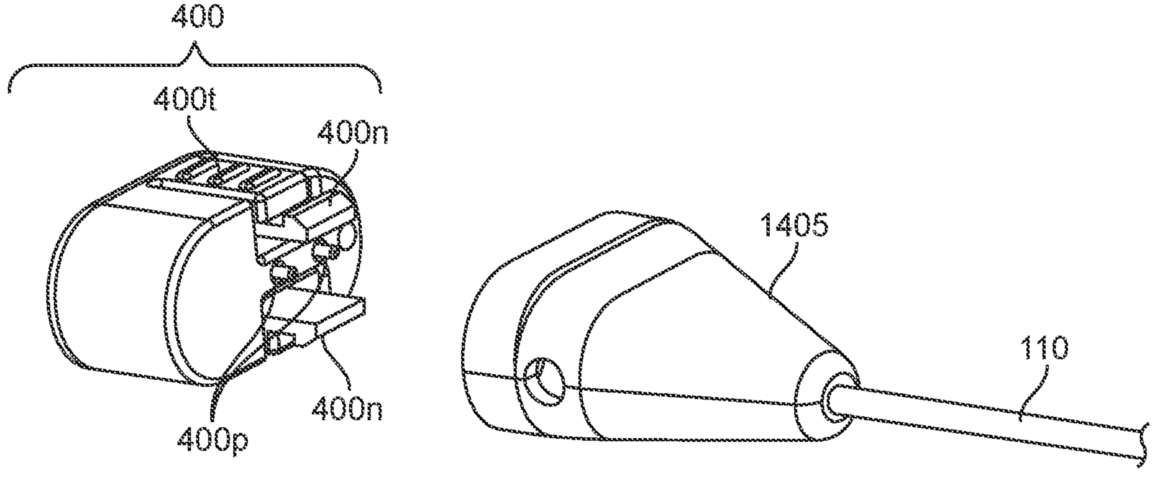

As shown in FIG. 16G, the pogo pins 440*p* on the miniature external generator 400 may connect to the conductor or contact pads 1540 on the handle hub 1405 in order to provide electrical current from the generator 400 to the distal electrodes on the lead body 110. Internally, the generator 400 can have one or more primary (non-rechargeable) or secondary (rechargeable) batteries and a printed circuit board assembly (PCBA) or other circuitry with digital and/or analog components. In one example, the generator may be powered by a primary coin cell battery with a cavity of at least 25 mAh. The batteries may power the PCBA or other circuitry which can sense the electrical signal(s) of the heart via the electrical connection to the distal electrodes and can provide active pacing by providing a current or voltage pulse train to the tissue via the electrical connection.

Figure 16H:
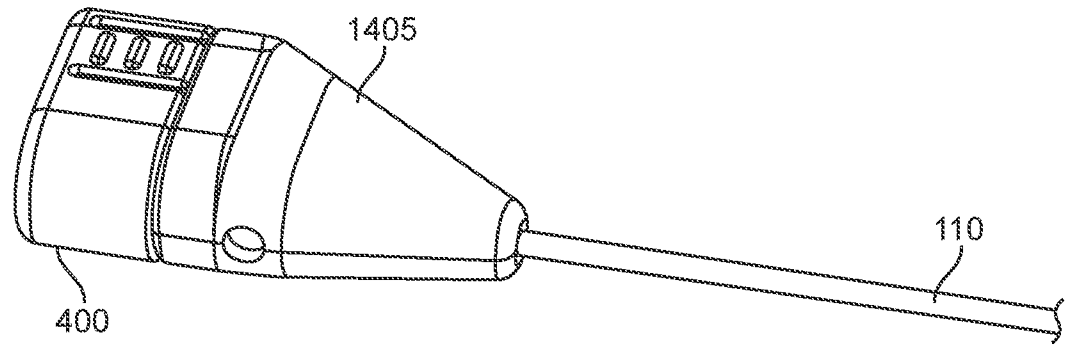

As shown in FIG. 16H, the miniature signal generator 400 may be connected to the handle hub 1405. The generator 400 can turn on automatically when it senses a lower resistance across the positive and negative electrodes. Alternatively or in combination, the generator 400 can be powered on manually via a mechanical tactile button on the generator 400. The generator 400 can then communicate, for example wirelessly via Bluetooth low energy (BLE) or other wireless communication protocol, to a smartphone or similar device and communicate clinically significant events (e.g., arrhythmias) and/or communicate the patient's electrocardiogram (ECG or EKG) in real-time.

Although the above steps show a method of operating a temporary pacing lead in accordance with embodiments of the present disclosure, a person of ordinary skill in the art will recognize many variations based on the teaching described herein. The steps may be completed in a different order. Steps may be added or deleted. Some of the steps may comprise sub-steps. Many of the steps may be repeated as often as beneficial to the operation of the temporary pacing lead.

Figure 17A:
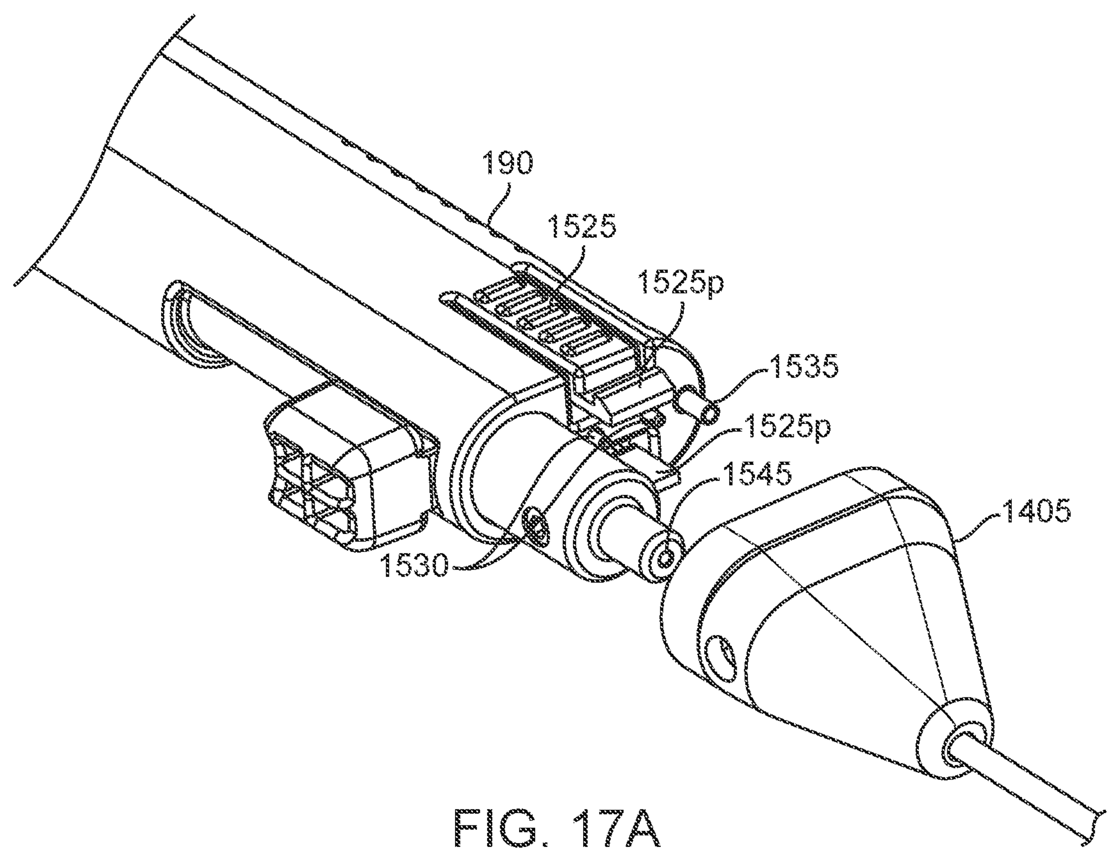
FIGS. 17A, 17B, and 17C show a front perspective view, front view, and back perspective view of the distal end of a detachable handle coupled to a handle hub coupled to a lead body of a temporary pacing device, according to embodiments of the present disclosure.
Figure 17B:
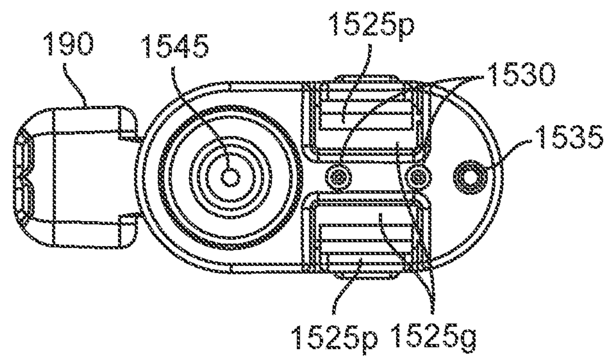
Figure 17C:
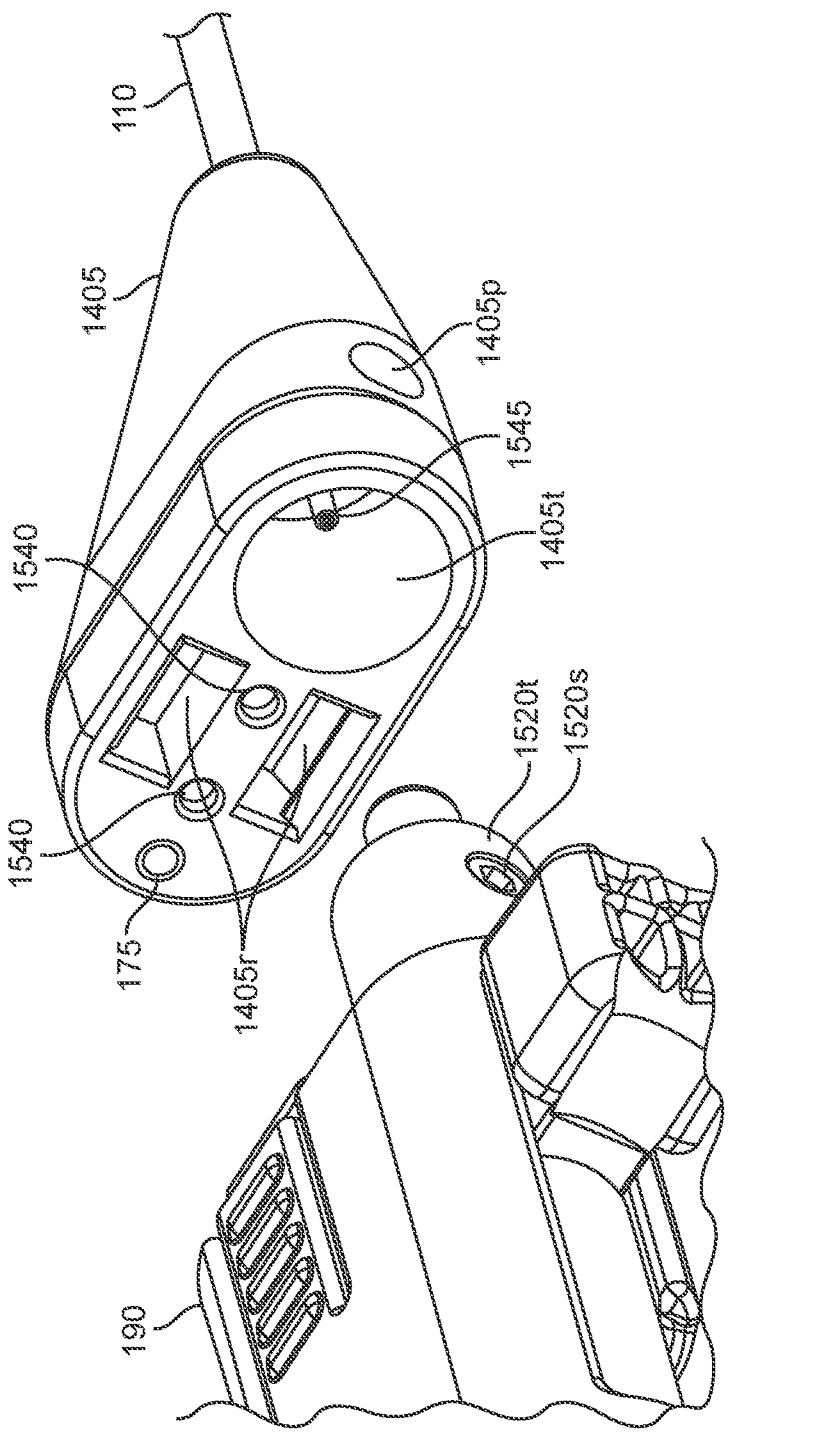

FIGS. 17A-17C show in detail the distal end of the detachable handle 190 with the handle hub or nose cone 1405. When the detachable handle 190 is connected to the handle hub or nose cone 1405, the tube adapter 1535 of the detachable handle 190 may fit into the inflation lumen 175 of the handle hub or nose cone 1405. The fit of the tube adapter 1535 into the inflation lumen 175 may be a tight fit to form an air tight seal. To maintain electrical connection from the connector pins of the (ring) electrodes at the distal end of the lead body 110, the pogo pin connectors 1530 may be mechanically pressed up against the conductor pads 1540 of the handle hub or nose cone 1405. Also, the connector snaps 1525*p* of the detachable handle 190 may fit into the recesses 1405*r* of the handle hub or nose cone 1405 and may thus connect or engage the detachable handle 190 to the handle hub or nose cone 1405. FIG. 17B shows air gaps 1525*g* adjacent the connector tabs 1525, which may provide room for the connector tabs 1525 to be depressed. As shown in FIG. 17C, the handle hub or nose cone 1405 may further comprise a set screw port 1405*p* and a shuttle track 1405*t*. The distal portion of the shuttle 1520*t* may fit within the shuttle track 1405*t* of the handle hub or nose cone 1405, and the set screw port 1405 may be aligned with the set screw 1520*s* on the shuttle 1520*t* to hold the shuttle 1520*t* in place.

Figure 18A:
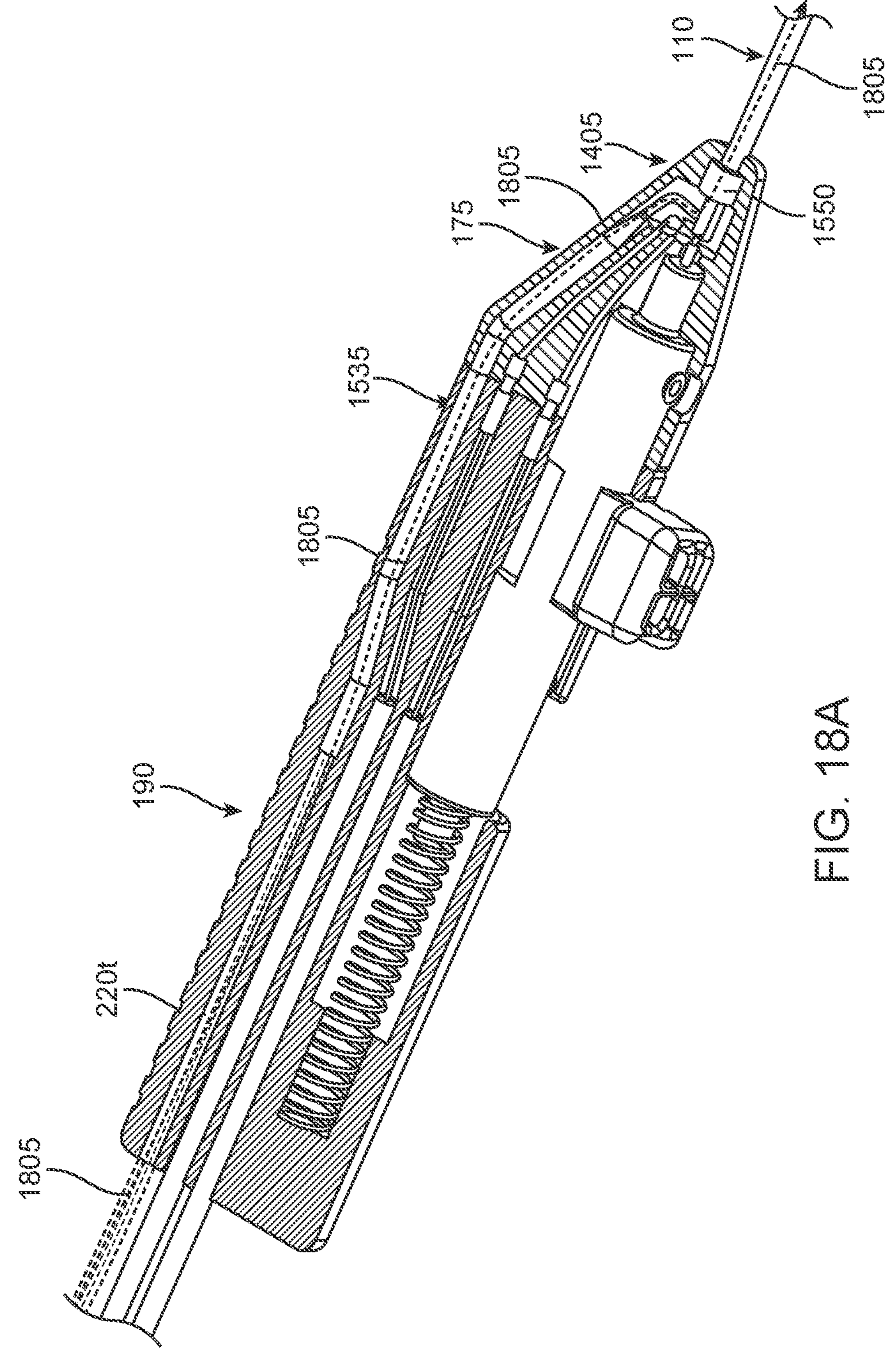
FIGS. 18A-18D show views of a detachable handle coupled to a handle hub coupled to a lead body of a temporary pacing device, according to embodiments of the present disclosure.
Figures 18B, 18C:
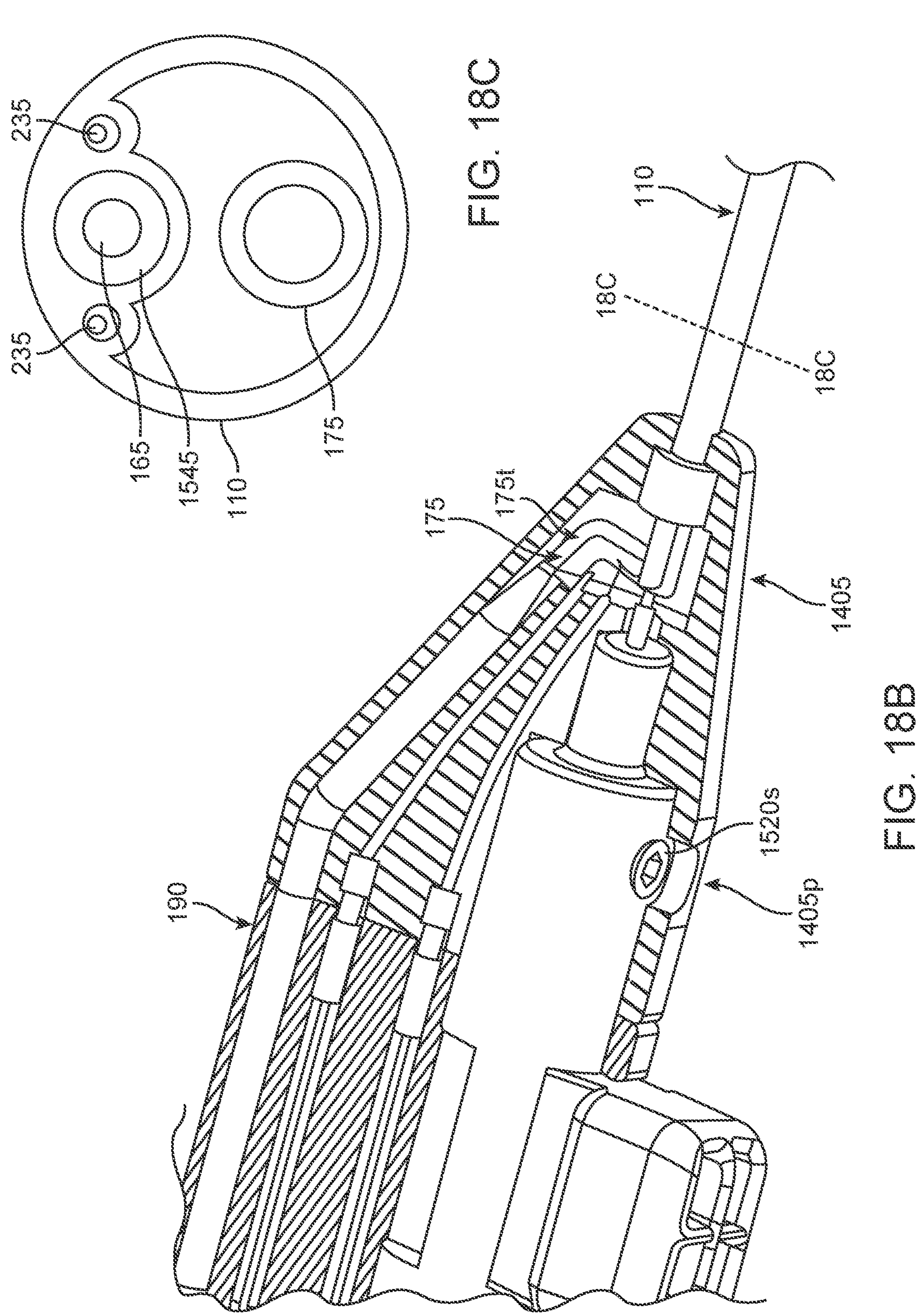
Figure 18D:
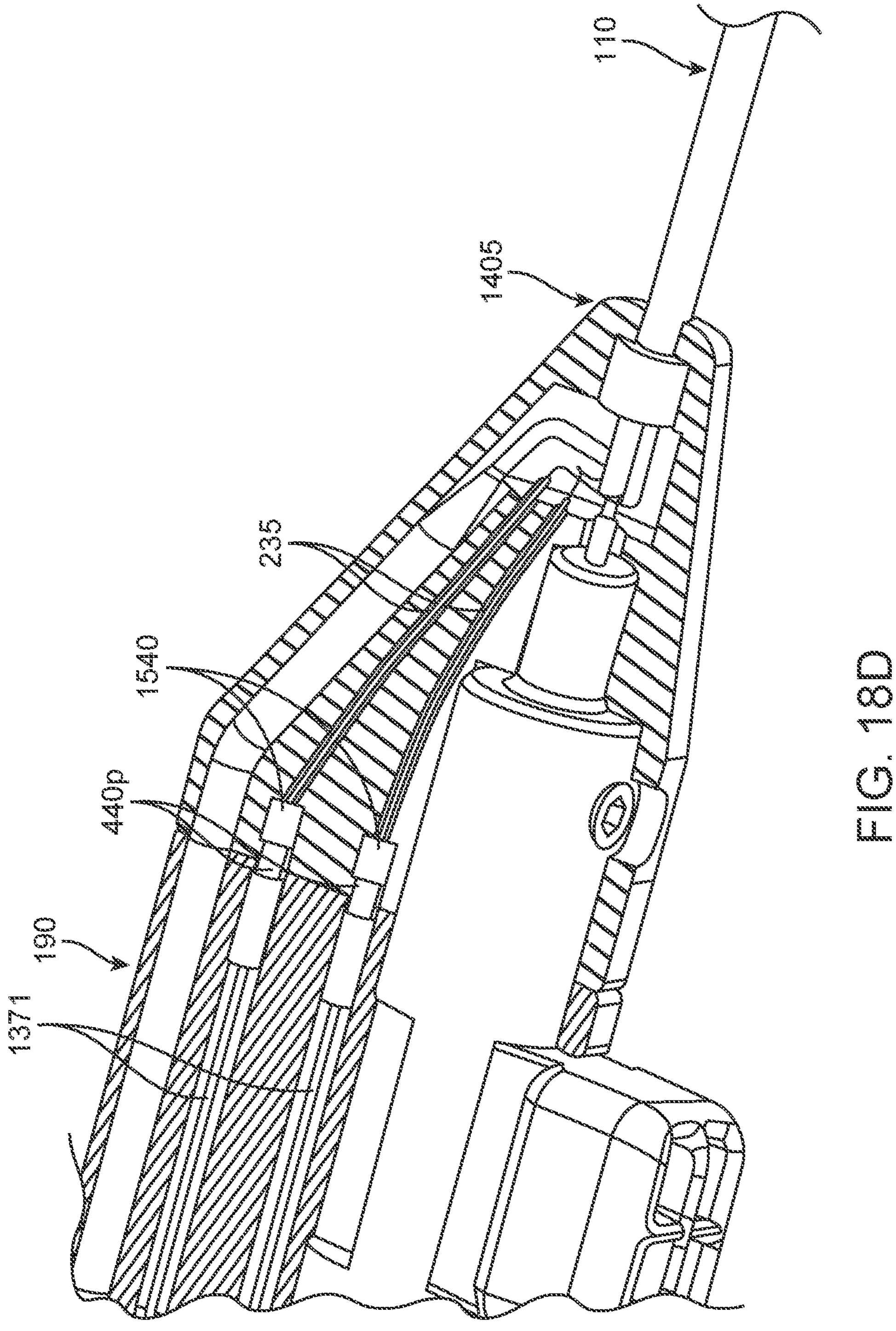

FIGS. 18A-18D show the detachable handle 190 coupled to the handle hub or nose cone 1405 which is coupled to the lead body 110. As shown in FIG. 18A, when the detachable handle 190 is connected to the handle hub or nose cone 1405, air can flow from the inflation port 220*p* to the balloon or displacement mechanism 170 at the distal end of the lead body 110 by traveling through the lumens illustrated by arrow 1805, including the inflation line 220*t*, the inflation adapter 1525, and the inflation lumen 175. As show in FIGS. 18B and 18C, the stabilizer wire adapter 1545 may be a hollow metal tube which may be permanently affixed to the stabilizer wire 165. The stabilizer wire adapter 1545 may have a larger diameter than the stabilizer wire 165 which may be advantageous because it can provide a larger surface area for the set screw 1520*s* to engage with when the handle 190 is attached to the handle hub or nose cone 1405. As shown in FIG. 18B, the handle hub or nose cone 1405 may further include a tapered section which can feed into the inflation lumen 175 at the lead body 110. FIG. 18C shows a cross-section of the lead body 110 taken across line 18C in FIG. 18B. As shown in FIG. 18D, to maintain electrical connection from the connector pins 440*p* to the (ring) electrodes on the distal end of the lead body 110, the connector or pogo pins 440*p* can be mechanically pressed up against the conductor pads 1540. The pogo pins 440*p* and the conductor pads 1540 may be gold or otherwise plated to minimize electrical contact resistance.

Figure 19A:
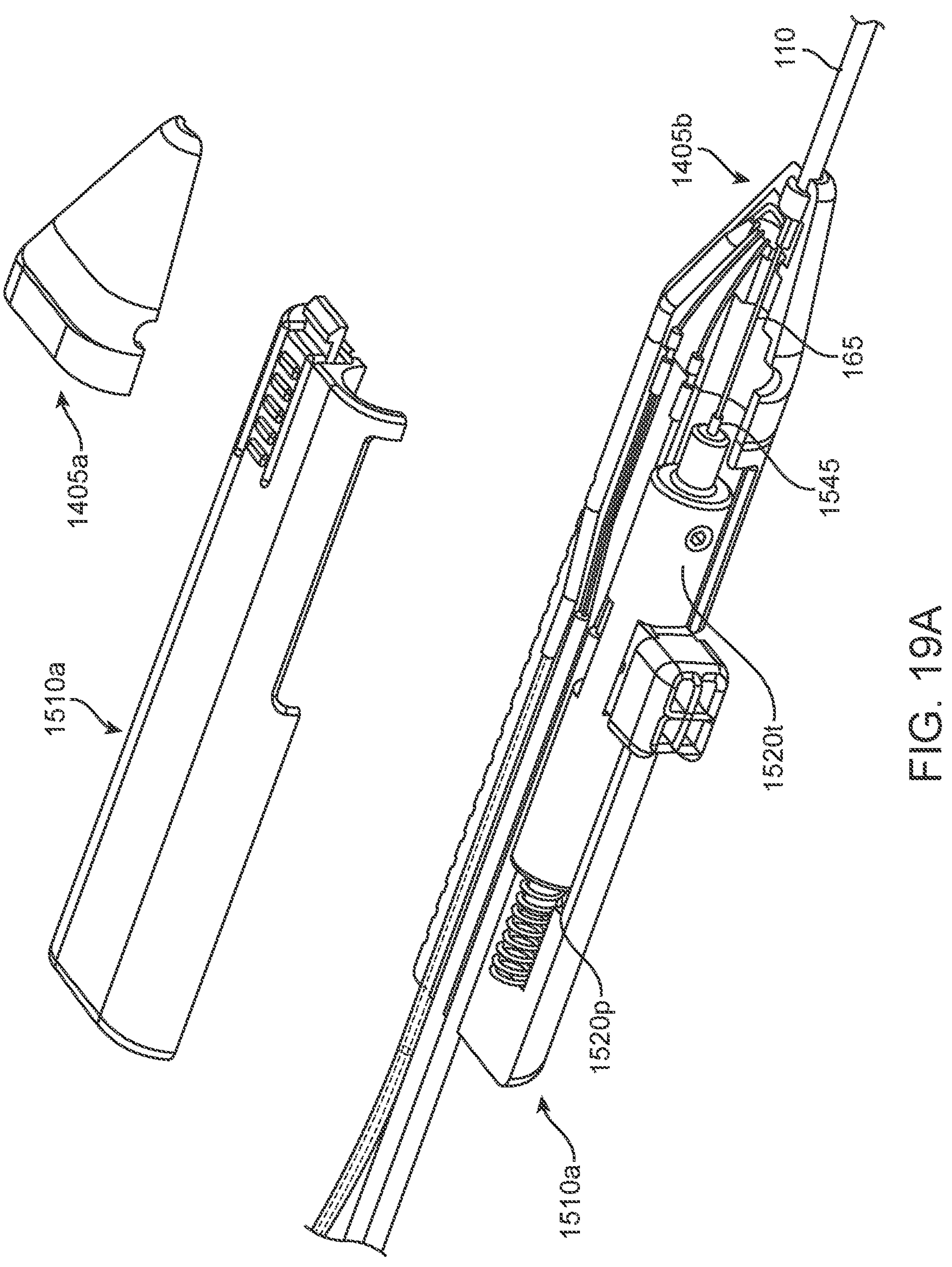
FIGS. 19A and 19B show exploded views of an assembly comprising a detachable handle coupled to a handle hub of a lead body of a temporary pacing device, with the shuttle retracted (FIG. 19A) and non-retracted (FIG. 19B), according to embodiments of the present disclosure.
Figure 19B:
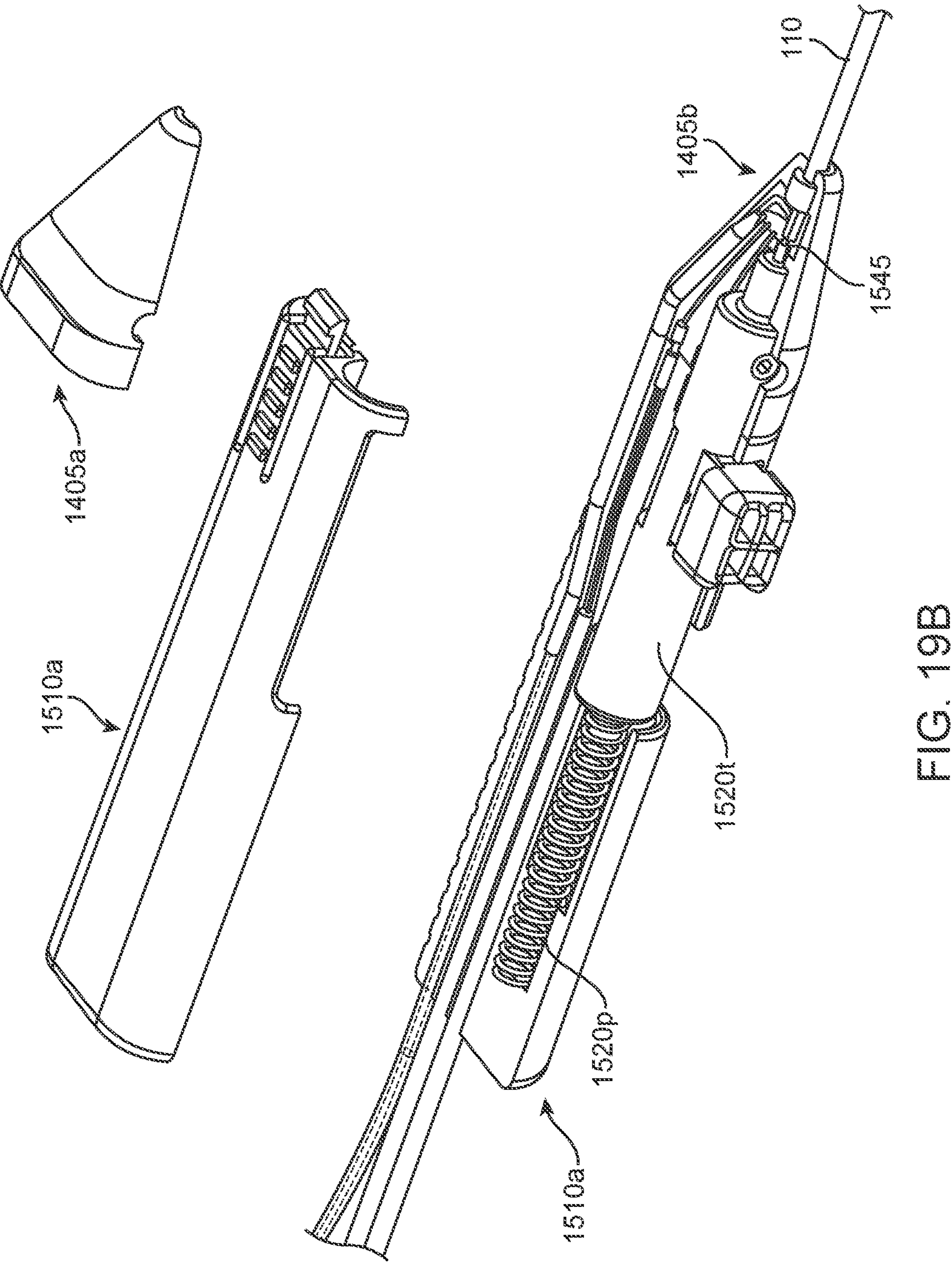

FIGS. 19A and 19B show an assembly comprising the detachable handle 190 coupled to the handle hub or nose cone 1405 which is coupled to the lead body 110. FIG. 19A shows the shuttle 1520*t* being retracted and the spring 1520*p* being compressed. FIG. 19B shows the shuttle 1520*t* being in a non-retracted state and the spring 1520*p* being uncompressed.

FIGS. 20A-20D show an assembly comprising the detachable handle 190 coupled to the handle hub or nose cone 1405 which is coupled to the lead body 110. When assembled, the distal end of the inflation line 220 can fit into the proximal end of the inflation adapter 1535 to form an air tight seal 1535*a*, the distal end of the inflation adapter 1535 can fit into the proximal end of the tube adapter 1535*t* to form an air tight seal 1535*b*, and/or the tube adapter 1535 can fit into the inflation lumen 175 to form a tight fit and an air tight seal 175*s*. When the set screw 1520 is tightened, the set screw 1520 can affix the stabilizer wire adapter 1545 and stabilizer wire 165 to the shuttle 1520*t* so that the stabilizer wire 165 can be retracted and deployed via the handle 190. When the set screw 1520 is loosened, the stabilizer wire adapter 1545 may no longer be affixed to the shuttle 1520*t*.

Figure 20A:
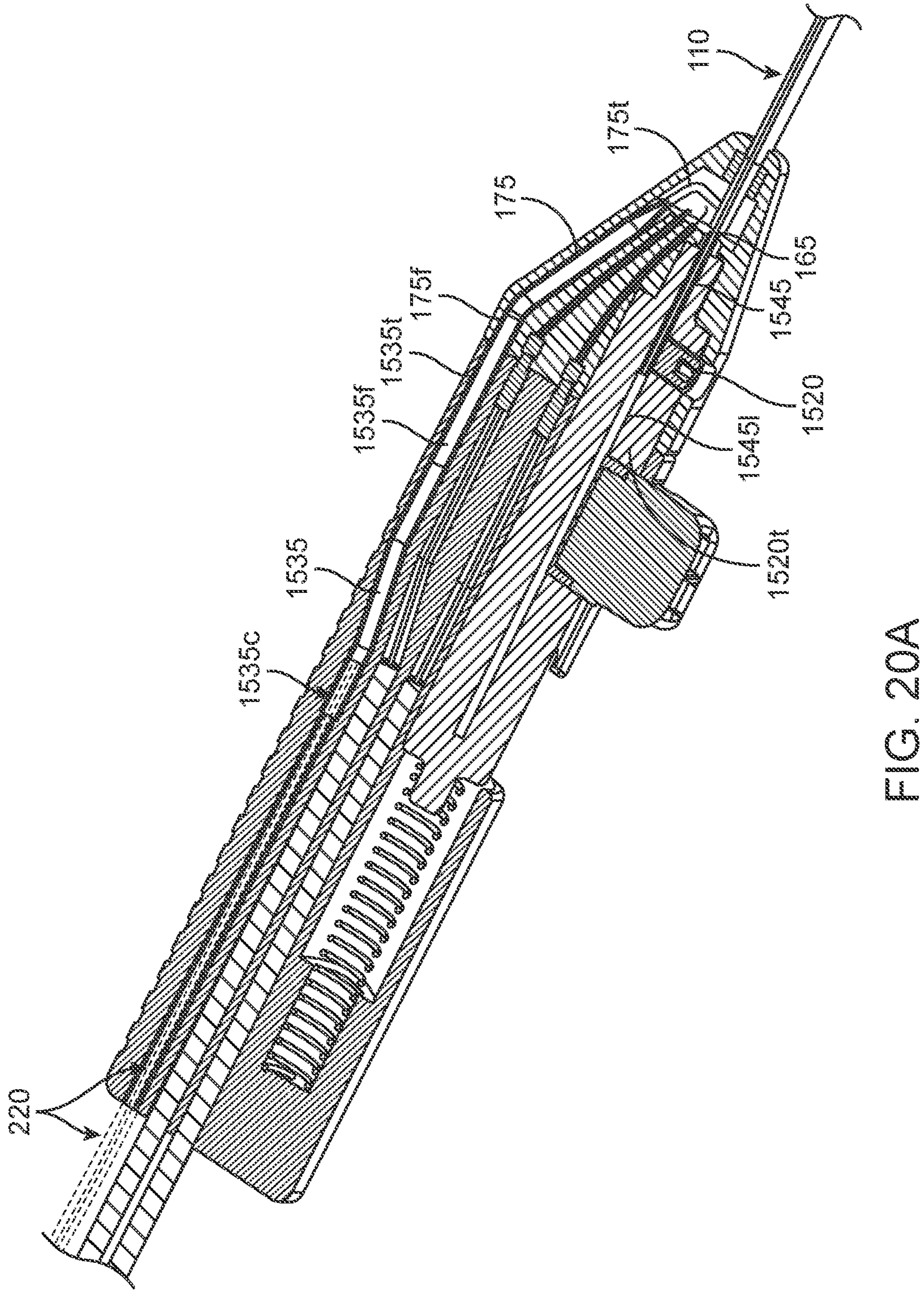
FIGS. 20A-20D show views of a detachable handle coupled to a handle hub coupled to a lead body of a temporary pacing device, according to embodiments of the present disclosure.
Figures 20B, 20C:
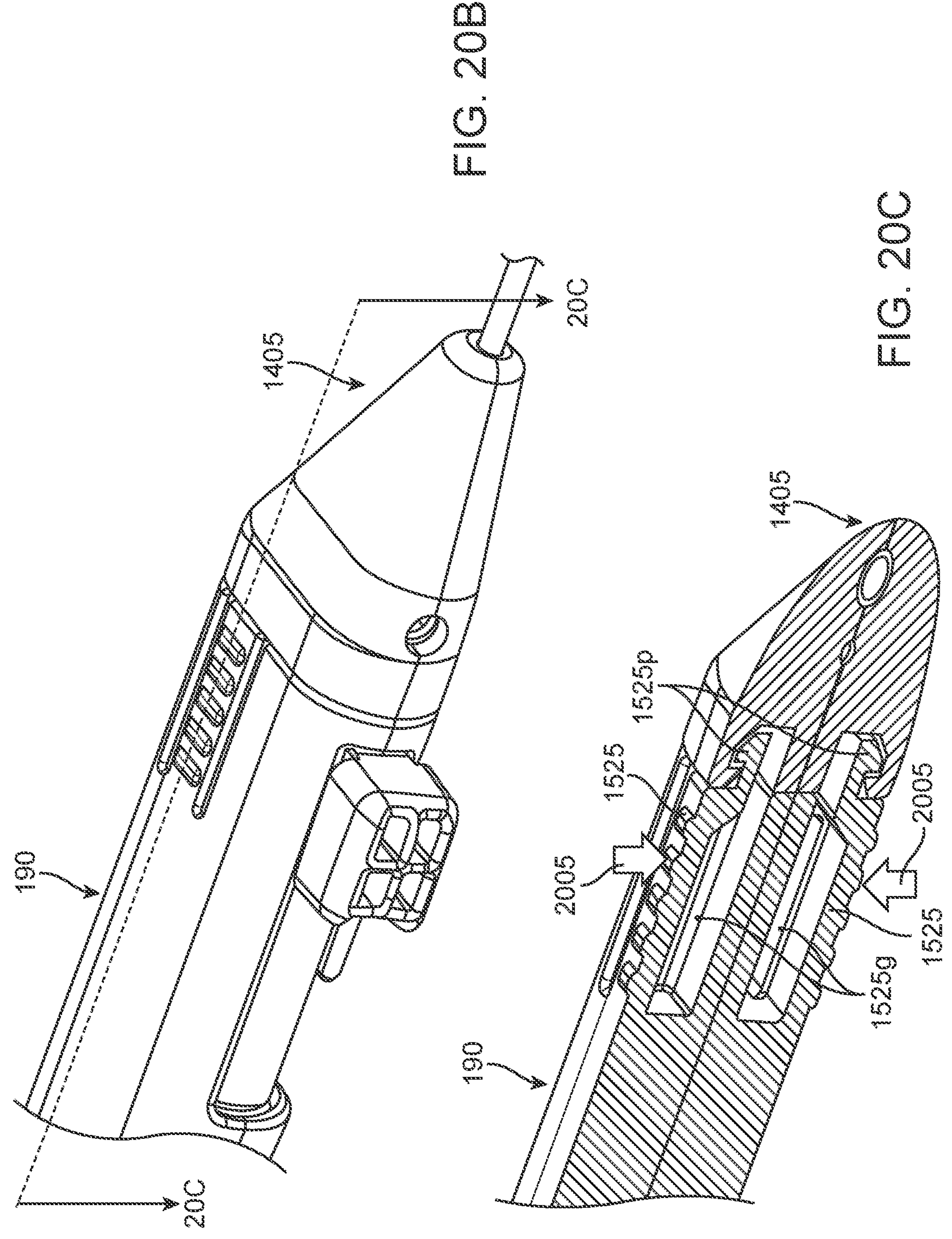

FIG. 20C shows a cross-section of the assembly taken through line 20C in FIG. 20B. The connector snaps 1525*p* of the detachable handle 190 may snap into and engage the detachable handle 190 to the handle hub or nose cone 1405. The connector tabs 1525 may be effectively cantilever beams so that when a user applies a force on the connector tabs 1525, as shown by arrows 2005, the connector tabs 1525 may displace into the air gap spaces 1525*g* which may allow the connector snaps 1525*p* to disengage from the handle hub or nose cone 1405.

Figure 20D:
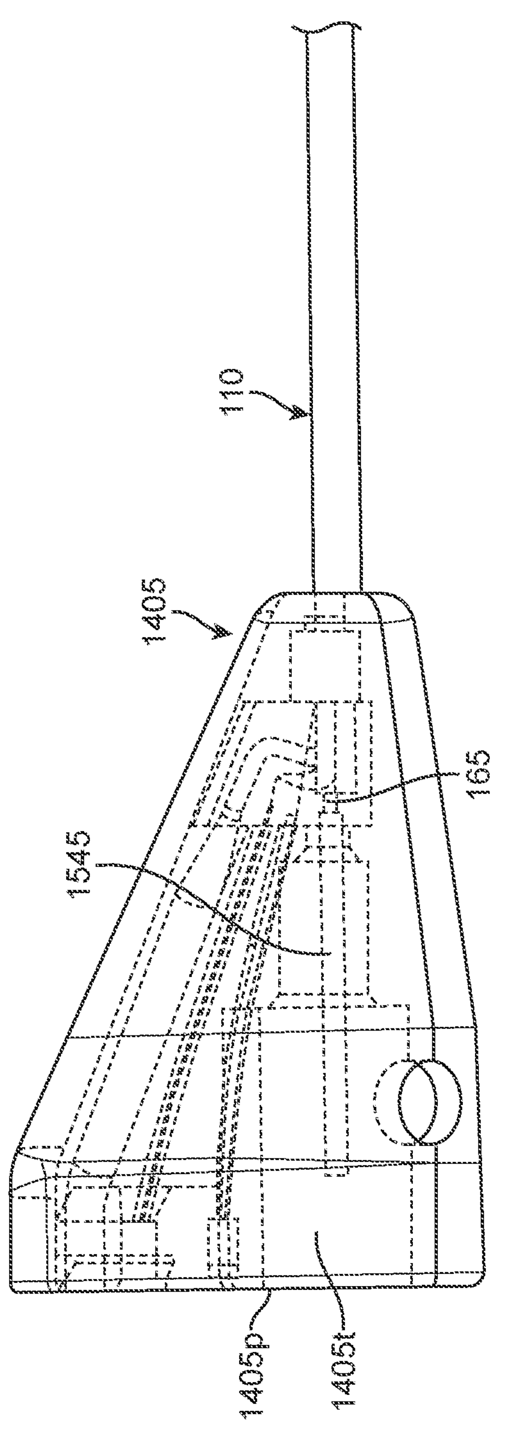

The stabilize wire adapter 1545 may comprise a hollow metal tube which may be permanently affixed to the stabilizer wire 165. The stabilizer wire adapter 1545 may have a larger diameter than the stabilizer wire 165 which may be advantageous because it can provide a larger surface area for the set screw 1520 to engage when the handle 190 is attached to the handle hub or nose cone 1405. When the detachable handle 190 is disengaged from the handle hub or nose cone 1405 as shown in FIG. 20D, the stabilizer wire 165 may be inserted from the proximal surface 1405*p* of the handle hub or nose cone 1405 in order to prevent external forces from being applied to the stabilizer wire adapter 1545.

FIGS. 21A to 21G show an exemplary method of operating the temporary pacing lead 100.

Figures 21A, 21B, 21C:
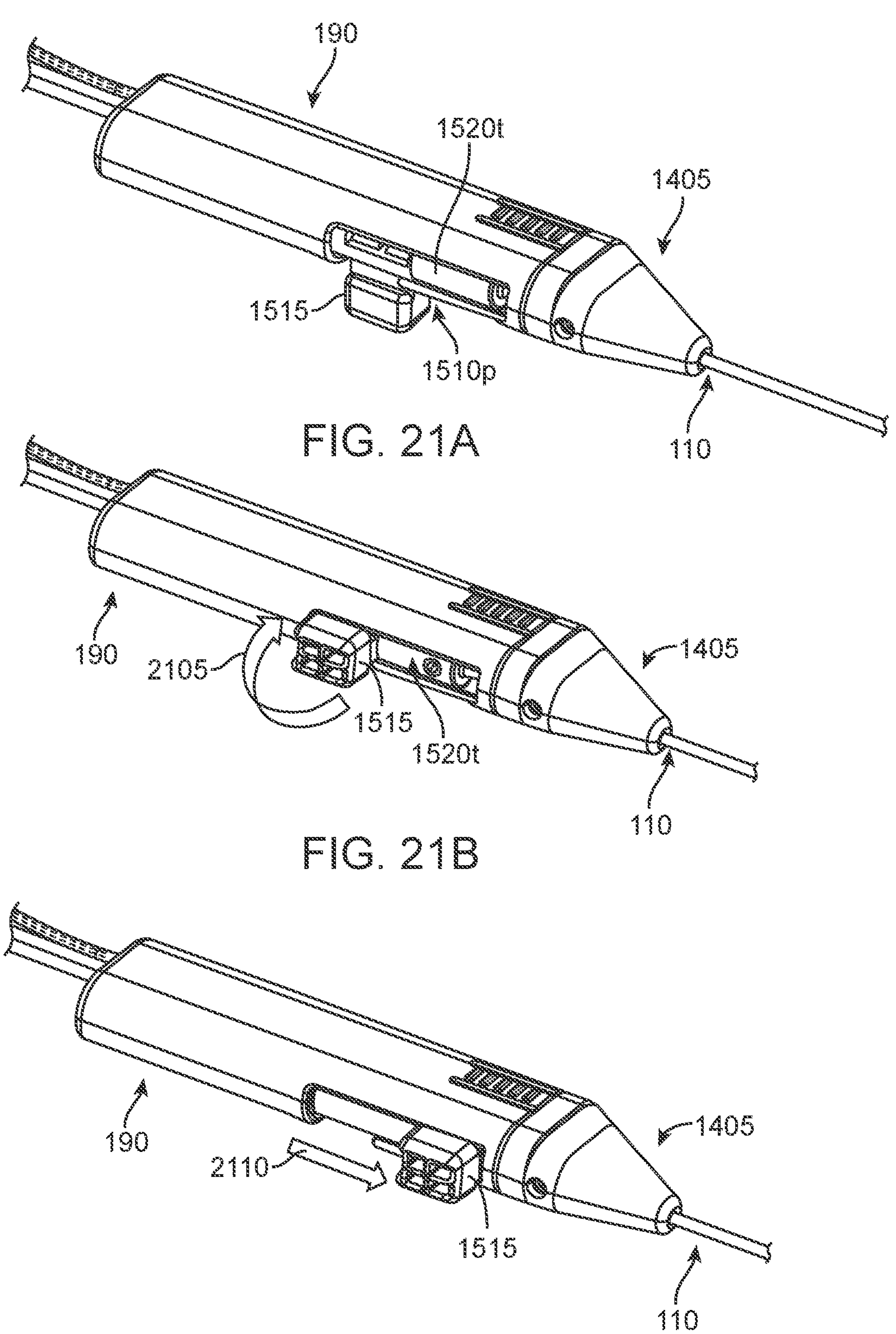
FIGS. 21A to 21G show an exemplary method of operating a temporary pacing device, according to embodiments of the present disclosure.

As shown in FIG. 21A, the deployment trigger 1515 may initially be in the retracted position, which may correspond to the stabilizer wires being in the retracted position and unexposed. The user may actuate the deployment trigger 1515 to deploy the stabilizer wires. The deployment trigger 1515 may be coupled to the shuttle 1520*t*. The shuttle 1520*t* may be compressing the spring 1520*p* that is located proximal to the shuttle 1520*t*. The spring 1520*p* may not be free to expand because the deployment trigger 1515 may be constrained from translating forward or distally due to the handle shell feature or stop 1510*p*.

As shown in FIG. 21B, when the user actuates the deployment trigger 1515 such as by rotation as shown with arrow 2105, the spring 1520*p* which is in the compressed position can be free to expand. As the spring 1520*p* expands linearly, it can linearly translate the shuttle 1520*t* and thus linearly translate the stabilizer wires.

As shown in FIG. 21C, as the shuttle 1520*t* travels forward in a direction indicated by arrow 2110, the stabilizer wire may travel forward until the stabilizer wires on the distal end of the lead body are fully exposed. FIG. 21C shows the deployment trigger 1515 in the final position when the stabilizer wires are fully exposed.

Figures 21D, 21E, 21F, 21G:
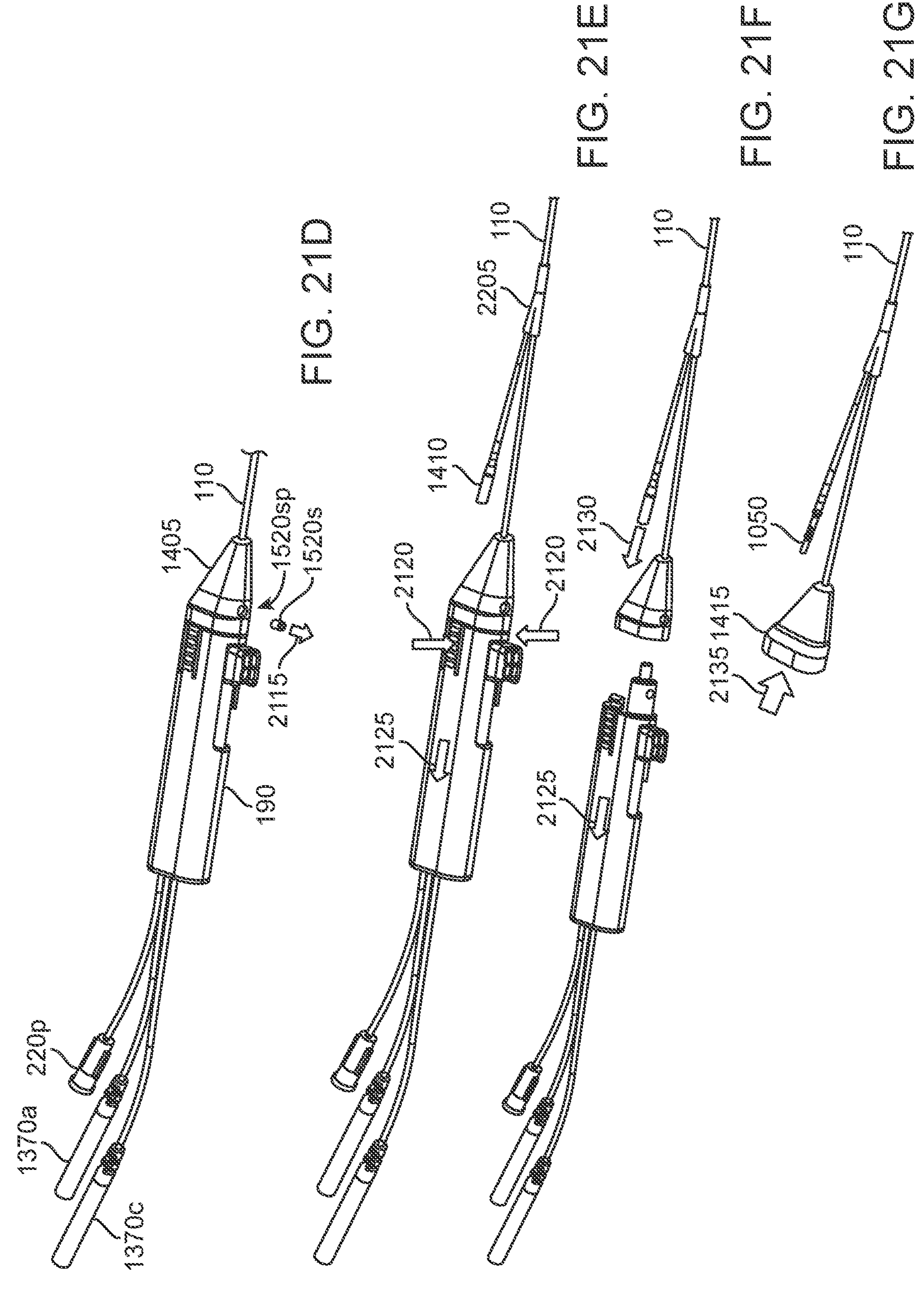

As shown in FIG. 21D, once the stabilizers are fully deployed, the user can connect the positive pin connector 1370*c* and the negative pin connector 1370*a* to an external generator. Once the user is done using the external generator, the user may disconnect the handle 190 from the lead body 110. The first step may be to remove the set screw 1520*s* via the set screw port 1520*sp* on the handle hub 1405 in the direction shown by arrow 2115.

As shown in FIG. 21E, to disengage the detachable handle 190 from the handle hub 1405, the user can simultaneously depress the connector tabs 1525 on both sides as indicated by arrows 2120 and retract the detachable handle 190 proximally as indicated by arrow 2125.

As shown in FIG. 21F, once the detachable handle 190 is disengaged from the handle hub 1405, the detachable handle 1910 can be removed from the handle hub 1405 and the lead body 110, for example, by being retracted in a direction indicated by the arrow 2125. The cap over the standard connector 1050 (such as an international standard connector interface, for example, IS-1) may be retracted as indicated by the arrow 2130 to expose the standard connector 1050.

As shown in FIG. 21G, the handle hub or nose cone cap 1415 may be placed over the handle hub or nose cone 1405 to protect the components located in the handle hub or nose cone 1405 (e.g., the conductor pad, stabilizer wire, inflation lumen, etc.) The exposed standard connector 1050 may comprise an IS-1 connector that is an international standardized connector and any external generator that can accept an IS-1 connector can be connected to it.

Although the above steps show a method of operating a temporary pacing lead in accordance with embodiments of the present disclosure, a person of ordinary skill in the art will recognize many variations based on the teaching described herein. The steps may be completed in a different order. Steps may be added or deleted. Some of the steps may comprise sub-steps. Many of the steps may be repeated as often as beneficial to the operation of the temporary pacing lead.

Figure 22:
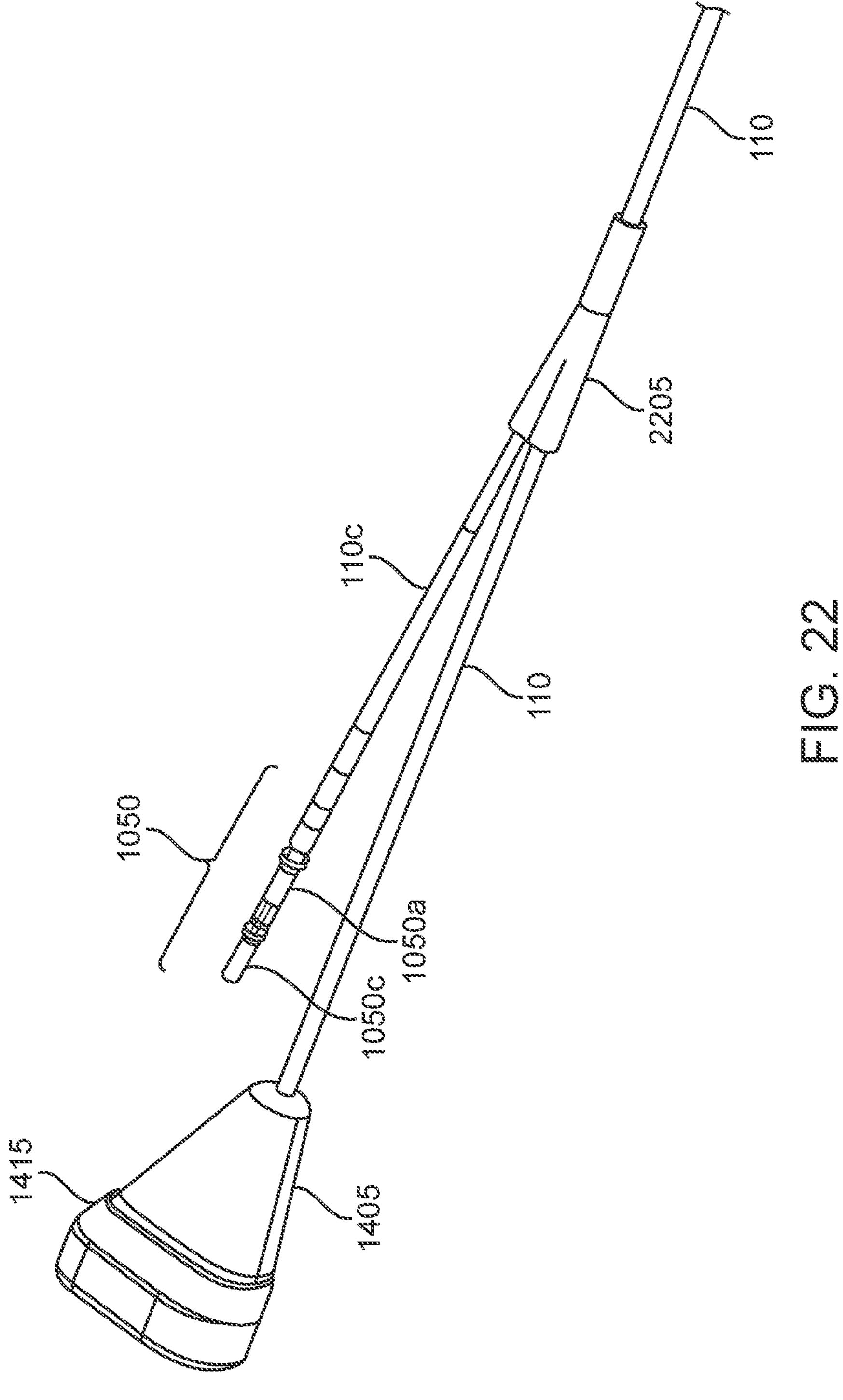
FIG. 22 shows a perspective view of a lead body of a temporary pacing device attached to a proximal cap, according to embodiments of the present disclosure.

FIG. 22 shows additional details of the proximal end of the lead body 110 of the temporary pacing device 100 coupled to a proximal (nose cone) cap 1415 placed over the handle hub or nose cone 1405. The proximal cap 1415 may be made of an elastic material (e.g., polyurethane, thermoplastic urethane, or thermoplastic elastomer) that the user can place over the proximal end of the handle hub or nose cone 1405 in order to protect the components located therein (e.g., the conductor pad, stabilizer wire, inflation lumen, etc.) from the ambient environment. The standard connector 1050 (such as an international standard connector interface, for example, IS-1) may comprise a positive terminal 1050*c* (e.g., an IS-1 cathode) and a negative terminal 1050*a* (e.g., an IS-1 anode), and the locations of the positive and negative terminals may be swapped. The temporary pacing device 100 may comprise a Y-connector 2205 to branch out a lead body 110*c* for the standard connector 1050.

Figures 23, 23A, 23B:
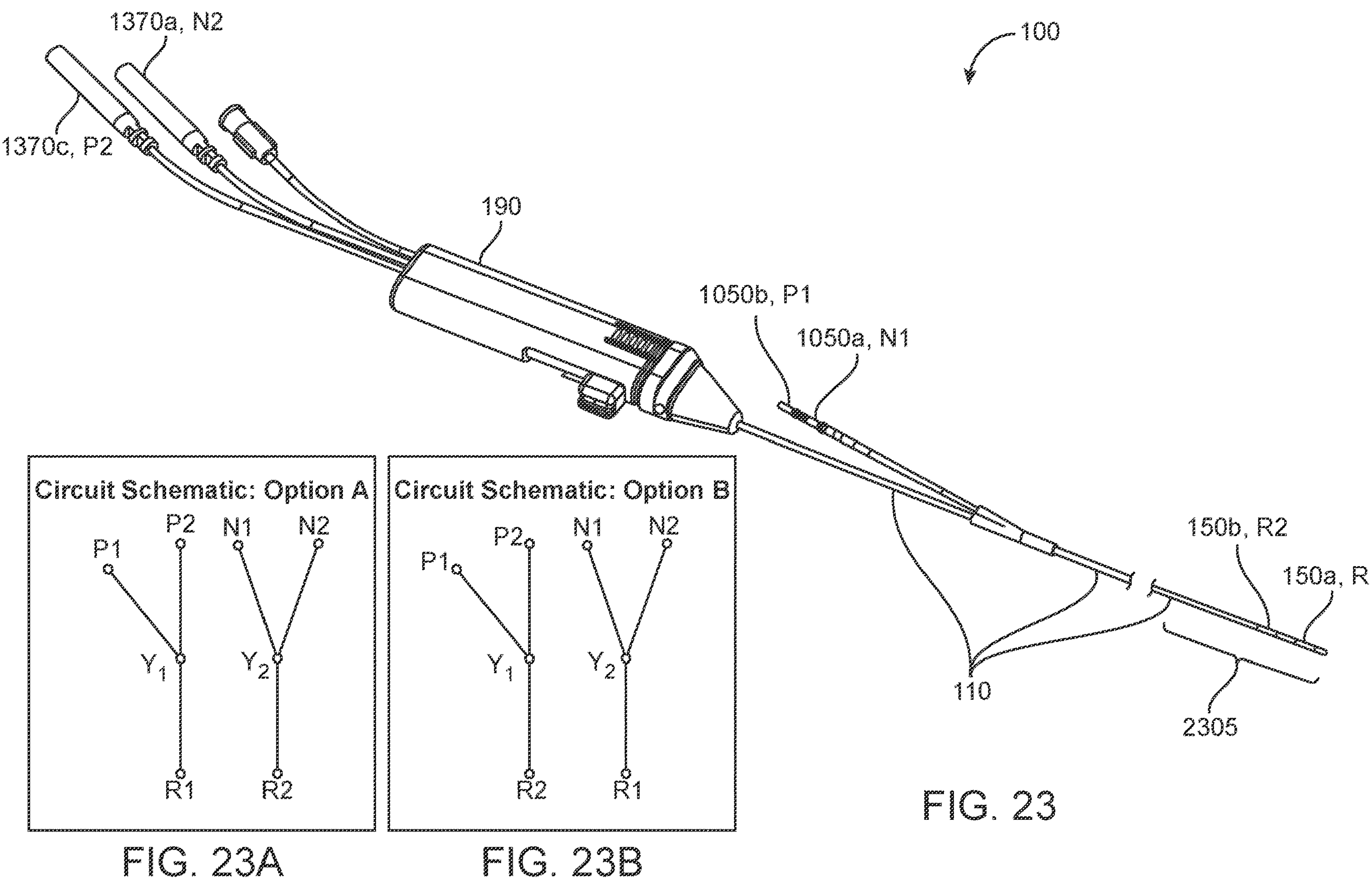
FIG. 23 shows a perspective view of a temporary pacing device adapted for use with a standard connector, according to embodiments of the present disclosure.
FIGS. 23A and 23B show circuit schematics for the temporary pacing device of FIG. 23.

FIG. 23A shows the temporary pacing device 100 with a standard connector 1050, including the portion 2305 of the lead body 110 suitable for implantation to the body of a patient. This implanted portion 2305 may include a first distal ring electrode 150*a* or R1 and a second distal ring electrode 150*b* or R2. The standard connector 1050 (such as an international standard connector interface, for example, IS-1) may comprise a negative terminal 1050*a* or N1 (e.g., an IS-1 anode) and a positive terminal 1050*n* or P1 (e.g., an IS-1 cathode) and, and the locations of the positive and negative terminals may be swapped if needed. The detachable handle 190 may be coupled to a negative pin connector 1370*a* or N2 and a positive pin connector 1370*c* or P2 which may be electrically coupled to the ring electrodes.

FIGS. 23A and 23B show circuit schematics for the temporary pacing device 100. In both, the resistance from node P1 to Y1 and P2 to Y1 and N1 to Y2 and N2 to Y2 may be roughly equal. For FIG. 23A, the resistance from Y1 to R1 and Y2 and R2 may be roughly equal. For FIG. 23B, the resistance from Y1 to R2 and Y2 to R1 may be roughly equal. In one example, in the case of FIG. 23A, the resistance from P1 to R1 may be 100 Ohms, the resistance from P2 to R1 may be 100 Ohms, the resistance from N1 to R2 may be 100 Ohms, and the resistance from N2 to R2 may be 100 Ohms.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

What is claimed is:

1. A method for positioning an electrode at target tissue of a patient's heart, said method comprising:

navigating an elongate body having a distal portion and a proximal portion to position an electrode array and at least one anchoring element carried on a side of the distal portion of the elongate body adjacent to the target tissue;

after the distal portion of the elongate body has been positioned, engaging the distal portion but not the proximal portion of the elongate body against the target tissue to contact the electrode array and the at least one anchoring element against the target tissue;

after engaging the distal portion of the elongate body against the target tissue, deploying the at least one anchoring element on the side of the distal portion of the elongate body to affix the at least one anchoring element to the target tissue;

coupling a first pacing signal generator to the proximal end of the elongate body, wherein the first pacing signal generator comprises a smaller profile than a second pacing signal generator that is solely external to the body of the patient;

delivering a pacing signal to the target tissue with the electrode array; and retaining the distal portion of the elongate body engaged against the target tissue for between 1 week and 180 days.

2. The method of claim 1, wherein the distal portion of the elongate body is engaged against the target tissue between 1 week and 30 days.

3. The method of claim 1, wherein the distal portion of the elongate body is engaged against the target tissue for between 1 week and 10 days.

4. The method of claim 1, further comprising retracting the at least one anchoring element, collapsing a displacement mechanism, and retracting the elongate body.

5. The method of claim 1, wherein a proximal portion of the elongate body extends out from the body of the patient after the distal portion of the elongate body is engaged against the target tissue.

6. The method of claim 5, further comprising operating a control handle coupled to the proximal portion of the elongate body to deploy the at least one anchoring element.

7. The method of claim 6, further comprising detaching the control handle coupled to the proximal portion of the elongate body after the distal portion of the elongate body is engaged against the target tissue.

8. The method of claim 5, further comprising coupling the second pacing signal generator to the proximal end of the elongate body.

9. The method of claim 8, wherein the second pacing signal generator is coupled to the proximal end of the elongate body with a standard interface.

10. The method of claim 9, wherein the standard interface is an IS-I interface.

11. The method of claim 5, further comprising coupling the first pacing signal generator and the second pacing signal generator to the proximal end of the elongate body and switching delivery of a pacing signal between the first and the second pacing signal generator.

12. The method of claim 11 wherein the first pacing signal generator comprises a standard connector interface and the second pacing signal generator comprises a standard temporary external pacemaker device.

13. The method of claim 5, further comprise coupling one or more of (i) a control handle to actuate one or more of the displacement member or the at least one anchoring element or (ii) the first pacing signal generator to an interface at the proximal end of the elongate body.

14. The method of claim 1, further comprising positioning the first pacing signal generator subcutaneously.

15. The method of claim 1, further comprising recording electrical signals from the target tissue with the electrode array.

16. The method of claim 15, further comprising transmitting the recorded electrical signals to a local computing device.

17. The method of claim 16, wherein the local computing device is a mobile computing device of the patient.

18. The method of claim 16, transmitting, with the local computing device, the recorded electrical signals to a remote computing device.

19. The method of claim 18, further comprising notifying a medical professional or caregiver with the remote computing device if the recorded electrical signals indicate an emergency or a clinically significant event.

20. The method of claim 19, wherein the remote computing device is a cloud-based server.

21. The method of claim 18, further comprising forwarding the recorded electrical signals to the medical professional or caregiver.

22. The method of claim 1, further comprising actuating a displacement mechanism attached to a side of the distal portion of the elongate body opposite to the side that carries the electrode array and the at least one anchoring element to engage the distal portion but not the proximal portion of the elongate body against the target tissue to contact the electrode array and the at least one anchoring element against the target tissue.

23. The method of claim 22, further comprising operating a control handle coupled to the proximal portion of the elongate body to actuate the displacement mechanism.

24. The method of claim 1, wherein the target tissue is cardiac tissue accessible from a cardiac chamber or epicardium.

* * * * *